(12) United States Patent
Milburn et al.

(10) Patent No.: US 6,586,218 B2
(45) Date of Patent: *Jul. 1, 2003

(54) COMPOSITIONS AND METHODS FOR INCREASING THE YIELDS OF IN VITRO RNA TRANSCRIPTION AND OTHER POLYNUCLEOTIDE SYNTHETIC REACTIONS

(75) Inventors: Susan C. Milburn, Austin, TX (US); Marianna Goldrick, Pflugerville, TX (US); Matthew Winkler, Austin, TX (US)

(73) Assignee: Ambion, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/966,062

(22) Filed: Sep. 28, 2001

(65) Prior Publication Data

US 2002/0177570 A1 Nov. 28, 2002

Related U.S. Application Data

(63) Continuation of application No. 08/323,602, filed on Oct. 17, 1994, now abandoned, which is a continuation of application No. 08/108,115, filed on Aug. 17, 1993, now abandoned, which is a continuation of application No. 07/810,968, filed on Dec. 20, 1991, now Pat. No. 5,256,555.

(51) Int. Cl.$^7$ .............................. C12N 9/14; C12N 9/10; C07H 21/04
(52) U.S. Cl. ................... 435/195; 536/25.3; 536/25.33
(58) Field of Search .................. 435/195; 536/25.3, 536/25.33

(56) References Cited

U.S. PATENT DOCUMENTS 4,683,202 A   7/1987   Mullis .......................... 435/91

FOREIGN PATENT DOCUMENTS

WO   WO 89/06700   7/1989
WO   WO 90/12111   10/1990

OTHER PUBLICATIONS

Cunningham and Ofegand, "Use of inorganic pyrophosphate to improve the yield of In Vitro Transcription reactions catalyzed by T7 RNApolymerase," *BioTechniques*, 9:713–714, 1990.

Gurevich et al., "Preparative in Vitro mRNA Synthesis Using SP6 and T7 RNA Polymerases," *Analytical Biochemistry*, 195:207–213, 1991.

Hall et al., "Structure of an unmodified tRNA molecule," *Biochemistry*, 28:5794–5801, 1989.

Krieg et al., "In Vitro RNA synthesis with SP6 RNA polymerases," *Methods in Enzymology*, 155:397–415, 1987.

Lizardi et al., "Exponential ampliction of nucleic acids: A new diagnostics using DNA replicases," *Trends in Biotechnology*, 9:53–58, 1991.

Milligan et al., "Synthesis of small RNA's using T7 RNA polymerase and synthetic DNA templates," *Nucleic Acids Research*, Published by IRL Press Ltd., Oxford, England, 15:8783–8799, 1987.

Pokrovskaya and Gurevich, "In Vitro Transcription: Preparative RNA yields in analytical scale reactions," *Analytical Biochem.*, 220:420–423, 1994.

Sambrook et al., "Molecular Cloning, A Laboratory Manual," Second Edition, CSH, Long Island, New York, pp. B10–B11, 1989.

Sampson et al., "Biochemical and physical characterization of an unmodified yeast phenylaline transfer RNA transcribed in vitro," *Proc. Natl. Acad. Sci. USA*, 85:1033–1037, 1988.

Weitzmann et al, "Cloning in vitro transcription, and biological activity of *Escherichia Coli* 23S ribosomal RNA," *Nucleic Acid Research*, 18:3515–3520, 1990.

Wyatt et al., "Synthesis and purification of large amounts of RNA oligonucleotides," !!!.

*Primary Examiner*—Jon P. Weber
(74) *Attorney, Agent, or Firm*—Fulbright & Jaworski L.L.P.

(57) ABSTRACT

The present invention relates to compositions and methods for increasing the yields of polynucleotide synthetic reactions. In particular, it relates to an improved reaction mixture for use in in vitro RNA trancription and in various other enzymatic reactions in which a polynucleotide is synthesised. The reaction mixture uses high concentrations of total nucleotides, in the order of 12 mM to 40 mM, i.e. levels that were previously thought to be inhibitory. Other useful modifications are also disclosed.

26 Claims, 3 Drawing Sheets

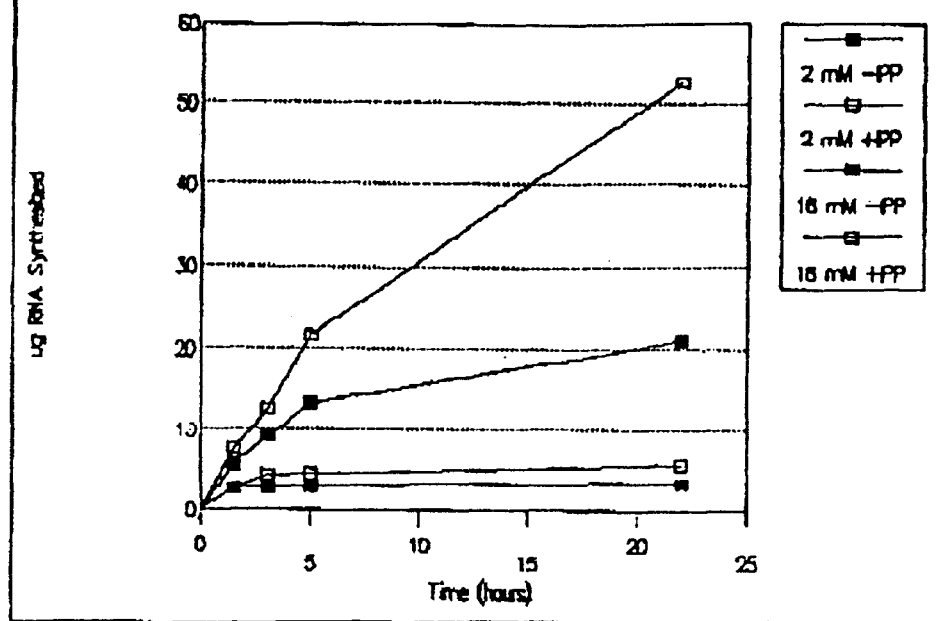

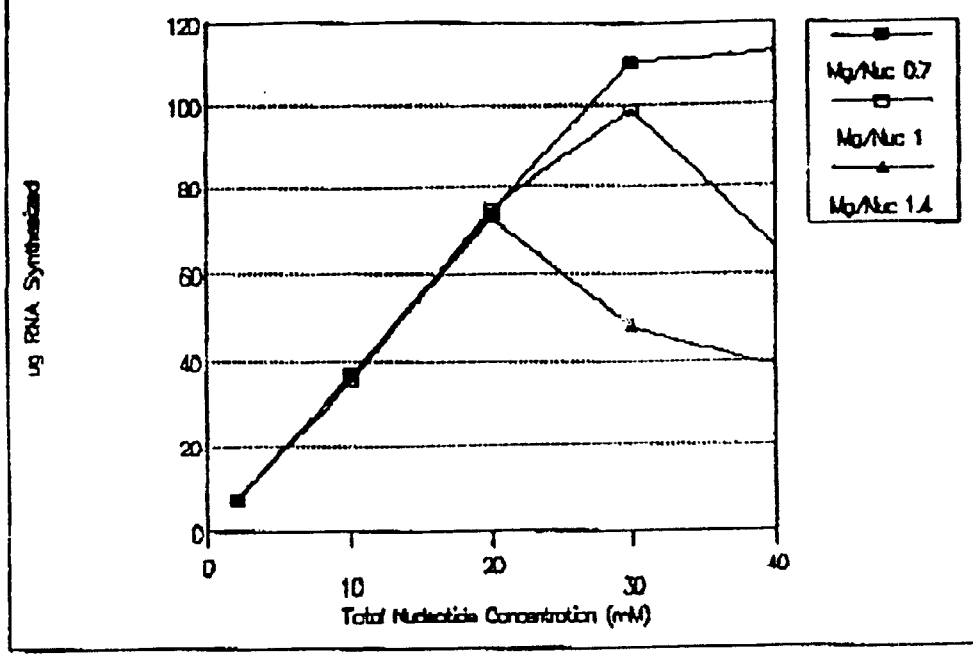

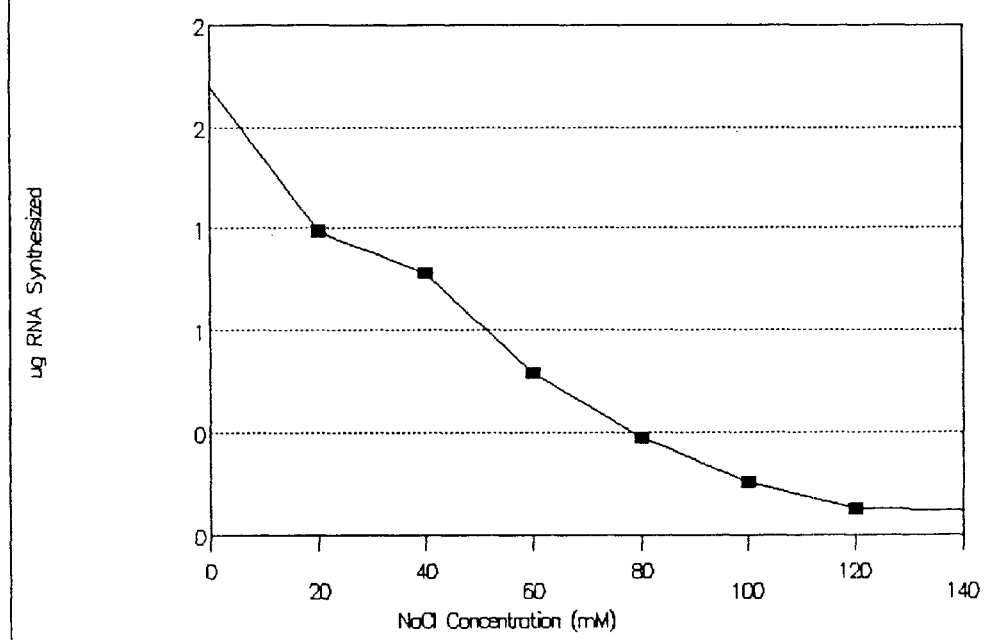

COMPOSITIONS AND METHODS FOR INCREASING THE YIELDS OF IN VITRO RNA TRANSCRIPTION AND OTHER POLYNUCLEOTIDE SYNTHETIC REACTIONS

This application is a continuation of application Ser. No. 08/323,602 filed Oct. 17, 1994, abandoned, which is a continuation of Ser. No. 08/108,115 filed Aug. 17, 1993, abandoned, which is a continuation of Ser. No. 07/810,968 fled Dec. 20, 1991, issued as U.S. Pat. No. 5,256,555 on Oct .26, 1993.

BACKGROUND OF THE INVENTION

1. Field of the Invention

This invention relates generally to techniques used in molecular biology. In particular, it relates to an improved reaction mixture for use in in vitro RNA trancription and in various other enzymatic reactions in which a polynucleotide is synthesised. The reaction mixture uses high concentrations of total nucleotides, at levels that were previously thought to be inhibitory; a concentration of $Mg^{++}$ that is subsaturating with respect to the nucleotide concentration, the enzyme inorganic pyrophosphatase, and most preferably, also $Mg^{++}$- or Tris-nucleotides.

2. Description of the Related Art

The techniques used in the field of molecular biology have been widely and successfully applied, not only in many areas of basic research, but also in providing solutions to several medical and agricultural problems. As such, molecular biology is of great importance to scientific research, medicine, human welfare and the economy.

RNA and DNA polymerization reactions, which result in the synthesis of RNA or DNA polynucleotides, are an integral part of a variety of techniques used in molecular biology. Obviously, an increase in the yield of these reactions would be beneficial, both in saving time and expense. Such reactions include, in vitro transcription reactions, amplification techniques such as the polymerase chain reaction (PCR), self-sustained sequence replication (3SR), QB replicase and others. These reactions often employ bacteriophage RNA polymerases, such as SP6, T7 and T3, for example, in the synthesis of both radiolabeled RNA probes and unlabeled RNA.

The rate of these synthetic reactions, and the amount of product formed, is known to be limited by several factors. A common belief in the art is that these limiting factors cannot generally be overcome, and that the yield of these reactions cannot be significantly increased. For example, it is thought that nucleotide concentrations greater than 8 mM are inhibitory to in vitro transcription reactions (Gurevich et al., 1991).

In principle, the yield of reactions can generally be increased by increasing the levels of substrate(s), in this case the concentration of nucleotides used in the reaction. However, in the synthesis of polynucleotides, high levels of the nucleotide substrate are known to act as competitive inhibitors of the polymerization reaction and actually decrease the yield of the reaction. They can also lead to increases in the error rate, which is highly undesirable. The $K_m$ for the nucleotide substrates are quite low (ATP, 47 $\mu$M; GTP 160 $\mu$M; UTP, 60 $\mu$M; CTP 81 $\mu$M) (Chamberlin and Ring, 1973). Thus, nucleotide concentrations in the mM range are likely to be saturating, and, as mentioned above, total nucleotide concentrations above 8 mM have been reported to inhibit RNA synthesis (Gurevich et al., 1991). It is likely that this inhibition is due to competitive inhibition of the polymerase by the high level of nucleotides. This phenomenon is discussed by Chamberlin & Rhodes (1974), in regard to E. coli RNA polymerase.

Considering the inhibitory effects that are believed to result from using high nucleotide concentrations, the total nucleotide concentrations currently used for reportedly optimal RNA synthesis range from 1.6–16 mM (Milligan et al., 1987; Sampson & Uhlenbeck, 1988; Cunningham & ofengand, 1990; Weitzmann, et al., 1990; Gurevich et al., 1991; Wyatt et al., 1991). It is particularly noteworthy that 'Current Protocols in Molecular Biology', a standard laboratory manual, recommends the lowest total nucleotide concentration, of 1.6 mM.

The substrate for polynucleotide synthetic reactions is actually a complex of the nucleotide with magnesium ions, i.e. a $Mg^{++}$-nucleotide ($Mg^{++}$-NTP), and therefore the magnesium concentration is also an important parameter. The conventional procedure is to routinely add magnesium at a concentration greater than the total nucleotide concentration. Indeed, the current view is that an excess of $Mg^{++}$ must be added in in vitro transcription reactions (Milligan & Uhlenbeck, 1989). It also been reported that a ratio of magnesium to total nucleotides of 1.75:1 is optimal (Wyatt et al., 1991).

The enzyme inorganic pyrophosphatase has recently been used in transcription reactions (Sampson & Uhlenbeck, 1988; Weitzmann et al., 1990; Cunningham & Ofengand, 1990), and DNA polymerase and DNA sequencing applications (Tabor & Richardson, 1990). The Cunningham and ofengand study concluded that the pyrophosphatase increases transcription yields and also minimizes the effect of variation of magnesium concentration, although this was not believed to be due to the pyrophosphate sequestering the $Mg^{++}$.

A further complication in polynucleotide synthesis is the fact that most phage polymerases have a low salt optima, SP6 polymerase in particular is very sensitive to even low levels of $Na^+$ (Butler & Chamberlin, 1982). Despite this, in most reactions of this nature nucleotide-salts are used, and in particular, $Na^+$-nucleotides. Indeed, most commercially available nucleotides are the $Na^+$, $Li^+$, $K^+$, $NH_4^+$ or $Ba^{++}$ salts. Increasing the levels of these nucleotides above those generally used would result in the introduction of amounts of salt which are inhibitory to the reaction.

SUMMARY OF THE INVENTION

The present invention seeks to overcome some of these and other drawbacks in the prior art by providing improved compositions for in vitro RNA trancription and various other enzymatic reactions in which a polynucleotide is synthesised. In particular, an improved reaction mixture is disclosed comprising high concentrations of total nucleotides, in the order of between about 12 mM and 40 mM, that were previously thought to be inhibitory; an effective molar concentration of $Mg^{++}$ that is subsaturating with respect to the molar total nucleotide concentration, the enzyme inorganic pyrophosphatase, and most preferably, also $Mg^{++}$- or Tris-nucleotides. The invention further relates to methods for employing this reaction mixture in various synthetic procedures.

As used herein, the term total nucleotide concentration is intended to refer to the total concentration of nucleotides (NTPs), i.e. the sum of the concentrations of ATP, GTP, CTP, and/or UTP, present initially in the reaction mixture when the various components of the reaction mixture have been assembled in the final volume for carrying out the reaction. Naturally, as the reaction proceeds, the nucleotides themselves will be incorporated into the polymer and so the concentration of total nucleotides will be progressively reduced from its initial value.

The process of synthesizing a polynucleotide is subject to substrate inhibition by the magnesium complexes of the various nucleotides, $Mg^{++}$-NTPs. Higher concentrations of $Mg^{++}$-NTPs slow the rate of polymerization as an excess of each of the other species inhibits the incorporation of the correctly matched nucleotide into the growing polymer. An important aspect of the present invention is to provide a means of increasing the total nucleotide concentration without inhibiting the reaction.

The present invention provides a reaction mixture in which the total nucleotide concentration is greater than 12 mM and not so high as to substantially inhibit the reaction to be performed. It is proposed that for most applications the upper limit nucleotide concentration will be about 100 mM, however, a higher upper limit may be appropriate under certain circumstances. For most applications, the nuclebtide concentration will be between 12 mM and about 40 mM. In preferred embodiments, the total nucleotide concentration will be between about 16 mM and about 40 mM, and more preferably, between about 20 mM and about 40 mM.

The inventors have provided other components for use in the present reaction mixture, and further adjusted the concentrations of the various constituents, such that these higher total nucleotide concentrations do not inhibit the reaction as one may expect, but in fact act to stimulate the total amount of product synthesized and possibly the rate of polymerization.

As the substrate for the polymerization reaction is the $Mg^{++}$-nucleotide complex, an effective concentration of $Mg^{++}$ is herein defined as one that will form a complex with the nucleotides in the reaction mixture to allow the polymerization reaction to procede.

The present inventors have determined that the use of effective $Mg^{++}$ concentrations that are subsaturating with respect to the total molar nucleotide concentration is particularly advantageous. To create a reaction mixture in accordance with the present invention in which the $Mg^{++}$ concentration is subsaturating with respect to the total nucleotide concentration, it is not necessary for the absolute $Mg^{++}$ concentration to be less than the total nucleotide concentration. The reason for this is that not all the $Mg^{++}$ ions in the reaction mixture will be available to form a $Mg^{++}$-NTP complex. For example, some of the $Mg^{++}$ ions may be sequestered by inorganic pyrophosphate, depending on its generation in the reaction. Therefore, a $Mg^{++}$ concentration that is subsaturating with respect to the total molar nucleotide concentration is herein defined as one that is not more than 10% greater than the total nucleotide concentration. However, in preferred embodiments, it is contemplated that the $Mg^{++}$ concentration used will be equal to the total molar nucleotide concentration, and even more preferably, that it will be less than the total molar nucleotide concentration.

Another parameter for assessing the $Mg^{++}$ in the reaction is to calculate the "free" $Mg^{++}$, as opposed to the total $Mg^{++}$. Naturally, in any solution, the "free" concentration of an ion will always be less than the total concentration. In this case, the total $Mg^{++}$ is all the $Mg^{++}$ introduced into the reaction, while free $Mg^{++}$ is that $Mg^{++}$ not bound to nucleotides, enzymes and other constituents in the reaction mixture. The free $Mg^{++}$ will therefore be dependent on the other constituents in the reaction mixture. To calculate the free $Mg^{++}$ in the reaction mixture, one would use a software program, such as Maxchelate, version 4.12, (Chris Patton, Hopkins Marine Station, Stanford University, Pacific Grove, Calif. 93950). This program uses the association constants for $Mg^{++}$ and nucleotides and takes into account the pH of the reaction which will affect the association constant. The inventors have used this program to calculate the free $Mg^{++}$ for the experiment shown in FIG. 2. The values for free $Mg^{++}$ are shown in Table 1 below. An example of this is a calculation that compares the free $Mg^{++}$ for the study shown in FIG. 2 to that of a study disclosed by Cunningham and Ofengard (1990).

TABLE I

Free $Mg^{++}$ Values 40 mM Tris pH 8.0

| Total Nucleotide Concentration (mM) | Total $Mg^{++}$ (mM) .7/1 (Mg/Nuc) | Free $Mg^{++}$ (mM) | Total $Mg^{++}$ (mM) 1/1 (Mg/Nuc) | Free $Mg^{++}$ (mM) | Total $Mg^{++}$ (mM) 1.43/1 (Mg/Nuc) | Free $Mg^{++}$ (mM) |
|---|---|---|---|---|---|---|
| 2 | 1.4 | .115 | 2 | .327 | 2.86 | .982 |
| 10 | 7 | .140 | 10 | .767 | 14.3 | 4.44 |
| 20 | 14 | .144 | 20 | 1.10 | 28.6 | 8.74 |
| 30 | 21 | .146 | 30 | 1.35 | 42.9 | 13.0 |
| 40 | 28 | .147 | 40 | 1.56 | 57.2 | 17.3 |

Cunningham and Ofengand
40 mM Tris pH 8.0

| Total Nucleotide Concentration (mM) | Total $Mg^{++}$ (mM) | Free $Mg^{++}$ (mM) |
|---|---|---|
| 10 | 8 | .224 |
| 10 | 18 | 7.87 |

As such, in certain embodiments, the present invention concerns a reaction mixture for the synthesis of a polynucleotide in which the "free" $Mg^{++}$ concentration is equal to or less than $2 \times 10^{-4}$ M.

A further important aspect of the present invention is the inclusion within the reaction mixture of the enzyme inorganic pyrophosphatase, which catalyzes the hydrolysis of inorganic pyrophosphate. Being a product of the reaction, inorganic pyrophosphate may function as an end product inhibitor to limit the rate of the polymerization. The addition of pyrophosphatase to the reaction mixture allows pyrophosphate to be removed and thus prevents its direct inhibitory action. Furthermore, the inventors believe that the pyrophosphate molecule sequesters the $Mg^{++}$ ions and prevents them from forming the concentrations of $Mg^{++}$-NTP substrate complexes which are inhibitory to the polymerase in the early stages of the reaction. However, later in the reaction, when the nucleotide levels have been depleted, removing pyrophosphate serves to free $Mg^{++}$ and promote $Mg^{++}$-NTP formation and thus allows polymer synthesis to occur with subsaturating levels of $Mg^{++}$.

Levels of inorganic pyrophosphatase: The concentration of inorganic pyrophosphatase in the reaction mixture is not believed to be particularly critical, so long as it is sufficient to catalyze the hydrolysis of pyrophosphate. The inventors contemplate that an amount of pyrophosphatase corresponding to between about 10 and about 50 international units (U)/ml of reaction mixture of enzyme activity may be used, and more preferrably, an amount corresponding to approximately 15 U/ml. One international unit of pyrophosphatase activity is defined as the amount of enzyme that will liberate 1.0 $\mu$M of inorganic orthophosphate per minute at pH 7.2 at 25° C.

A further aspect of the present invention relates to the form in which the nucleotides are added to the reaction mixture. The inventors contemplated that the use of nucleotides in the form of a salt with $Na^+$, $K^+$, $Ba^{++}$, or $NH_4^+$, as commonly-used, may lead to the inhibition of the polymerization reaction by the counter ions. Therefore, in certain embodiments, it is proposed that the nucleotides may be added to the reaction mixture in a form other than as a compound with $Na^+$, $K^+$, $Ba^{++}$, or $NH_4^+$, such as a $Mg^{++}$-nucleotide or a Tris-nucleotide. The use of $Mg^{++}$- or [Tris-(Tris(hydroxymethyl)aminomethane] nucleotides is thought to be particulary advantageous when using SP6 polymerase. However, the present invention is not limited solely to the use of $Mg^{++}$- or Tris-nucleotides, as certain advantages will result from the use of the above-described reaction mixture irrespective of the form in which the nucleotides are added. For example, many basic compounds will be suitable counter ions for nucleotides. Possible examples include glycylglycine, Tricine or Bicine.

Of course, other components in addition to those described above will need to be added to the reaction mixture in order to achieve polynucleotide synthesis. One will wish to provide a buffered solution of a suitable ionic strength and pH and a reducing agent, such as 40 mM Tris-HCl, 10 mM dithiothreitol (DTT), 2 mM spermidine-HCl, pH 8.0. Naturally, one will ultimately need to include a polymerase enzyme and a linearised polynucleotide template for the polymerase to use in synthesizing the complementary nucleotide strand. It is also considered to be advantageous to include a component to limit the degradation of the polynucletide, such as a ribonuclease inhibitor.

The reaction mixture of the present invention will find particular utility in in vitro RNA transcription reactions. However, in certain embodiments, the present invention also relates to the preparation of both polyribonucleotides and polydeoxyribonucleotides using other methods. In the former case, the enzyme used in conduction with the reaction mixture will be an RNA polymerase, and in the latter, it will a DNA polymerase. The invention is not limited to the use of any particular polymerase enzyme. Indeed, it is contemplated that any enzyme, either of bacteriophage- or non phage-origin, that catalyzes the formation of a polynucleotide will be suitable. However, certain RNA or DNA polymerases are contemplated to be of particular use in accordance with the present invention. For example, RNA polymerases such as T7, or T3, or SP6 RNA polymerase; and DNA polymerases such as Taq, or T7 or T4 polymerase, or Klenow polymerase.

The present inventors have discovered that the use of higher concentrations of total nucleotides in conjunction with the above-described reaction mixture results in unexpectedly large increases in the formation of a polynucleotide. For example, standard yields achieved in RNA synthesis are generally on the order of 10–20 moles of product per mole of template (Xrieg and Melton, 1987). Significantly higher yields have been reported by other workers. For example, Cunningham and Ofengand, (1990) reported 627 moles of product per mole of template using T7 RNA polymerase. It is difficult, however, to directly compare yields from different laboratories because the different templates used have different intrinsic transcriptional efficiencies. Using T7 RNA polymerase, the present inventors compared the transcriptional yields using the conditions described by Cunningham and Ofengand, (1990) and our conditions described in the legend to FIG. 2. After a 6 hour incubation, the yield with the Cunningham and Ofengand, (1990) conditions was 196 moles of product per mole of template. With our best conditions, the yield was 561 moles of product per mole of template, which represents more than a 2.5 fold improvement. This experiment is shown in Table 3. Thus, the creation of conditions which allow nucleotide concentrations that were previously thought to be inhibitory to be used successfully has yielded unexpected benefits.

In certain embodiments, the invention relates to methods of preparing a polynucleotide using the reaction mixture of the present invention. As mentioned above, the reaction mixture is believed to be particularly suitable for use in in vitro RNA transcription reactions. To synthesize an RNA molecule in this manner, one would prepare a reaction mixture as described above, add to it a polynucleotide template and an RNA polymerase enzyme, and incubate the reaction mixture. Either radioactively labeled polynucleotides, for use as probes, or unlabeled polynucleotides may be prepared, by using labeled or unlabeled substrate nucleotides.

In further methodological embodiments, the above-described reaction mixture may be used in other polynucleotide synthetic reactions. Methods of this sort are intergral parts of several commonly-used techniques in molecular biology apart from in vitro RNA transcription, these include amplification techniques such as polymerase chain reaction (PCR), self-sustained sequence replication (3SR), QB replicase and others. In each of these techniques, increases in the yield of the reaction would be beneficial. It is proposed that the present invention provides a means that this may be achieved by using the reaction mixtures disclosed herein. Furthermore, the invention is not limited to reactions in which a polymerase enzyme is used. For example, other techniques that could benefit from using the present reaction mixture include the DNA and RNA ligase reactions in which ATP is hydrolysed to AMP and pyrophosphate.

BRIEF DESCRIPTION OF THE DRAWINGS

FIG. 1. Comparison of high and low nucleotide concentrations, plus and minus pyrophosphatase on RNA synthesis.

Reactions were carried out with 50 $\mu$g/ml linearized template DNA (Xef1 template which codes for a 1.7 kb RNA transcript), $2 \times 10^3$ U T7 RNA polymerase/ml, 1250 U/ml human placental ribonuclease inhibitor and 15 U/ml of yeast inorganic pyrophosphatase where indicated. The buffer is 20 mM NaCl, 40 mM Tris-HCl (pH 7.8), 2 mM spermidine-HCl and 10 mM DTT. For 18 mM total nucleotides (4.5 mM A+C+G+U=18) the concentration of $MgCl_2$ was 16 mM. At 2 mM nucleotides the $MgCl_2$ concentration was 6 mM. The reaction volume was 20 µl and was incubated for the indicated times at 37° C. Reaction A was 2 mM NTPs, 6 mM $MgCl_2$. Reaction B was the same as A, but contained pyrophosphatase (IPP). Reaction C was 18 mM NTPS, 16 mM $MgCl_2$. Reaction D was the same as C, but contained pyrophosphatase (IPP).

FIG. 2. The effect of Nucleotide and $Mg^{++}$ concentration on RNA synthesis.

Reactions were carried out in the presence of varying ratios of nucleotides to $Mg^{++}$ (1:0.7, 1:1, 1:1.43). All reactions were carried out with 50Ag/ml linearized template DNA (Xef1 template), $2 \times 10^3$ U/ml T7 RNA polymerase, 1250 U/ml human placental ribonuclease inhibitor and 15 U/ml of yeast inorganic pyrophosphatase. The buffer was 40 mM Tris-HCl (pH 8.0), 2 mM spermidine-HCl and 10 mM DTT. The reaction volume was 20 µl and was incubated for 6 hours at 37° C. One µl aliquots were diluted into 400 µl of 1 mg/ml salmon sperm DNA and liquots were counted for total cpm and acid precipitable cpm to determine µg of RNA synthesized.

FIG. 3. The effect of $Na^+$ concentration on the activity of SP6 RNA polymerase.

The reaction conditions were 40 mM Tris-HCl (pH 7.5), 6 mM $MgCl_2$, 2 mM spermidine, 10 mM DTT, 1250 U/ml RNase Inhibitor, 1000 U/ml SP6 polymerase, a total nucleotide concentration of 2 mM ($4 \times 0.5$ mM A, C, G, U), and 1 µg linearized template DNA. The reaction volume was 20 µl and the incubation time at 37° C. was 3 hours.

DETAILED DESCRIPTION OF THE PREFERRED EMBODIMENTS

The current invention provides a reaction mixture for use in maximizing the yield of RNA or DNA polynucleotides produced in enzymatic reactions. Such reactions include those catalyzed by RNA and DNA polymerase and those catalyzed by RNA and DNA ligase in which ATP is hydrolyzed to yield AMP and pyrophosphate.

The reaction mixture of the present invention is particularly useful in conducting in vitro RNA transcription. The RNA polymerase enzymes widely used in this procedure are bacteriophage enzymes, typically from SP6, T7, and T3 bacteriophages. The in vitro RNA synthesis is directed by DNA templates cloned into plasmid vectors which contain the corresponding SP6, T7, or T3 promoters. By digesting the template with a restriction enzyme that cleaves distal to the phage promoter, a "run-off" transcript of a defined size can be synthesized. The SP6, T7, and T3 RNA polymerases have a high specificity for their respective 23 bp promoters. Most modern multi-purpose cloning vectors contain two different opposing phage promoters flanking a multiple cloning site. The high promoter specificity of the RNA polymerases allows transcription of one strand of the template with virtually no transcription from the promoter on the opposite strand.

In vitro transcription reactions are typically used for two distinct purposes. The first use is the synthesis of high specific activity RNA probes, using radioactively labeled nucleotides as substrates. The second purpose is the synthesis of larger amounts of unlabeled or low specific activity RNA for a variety of molecular biological uses which may benefit greatly by the use of the reaction mixture disclosed herein. These include, but are not limited to, in vitro translation studies, antisense RNA experiments, microinjection studies, and the use of RNA in driving hybridization reactions for the construction of subtractive cDNA libraries, and the like.

In large-scale transcription reactions, the concentration of total nucleotides currently used is high, well above the $K_m$ for the enzyme. While conventional transcription reactions of this sort can be used for the synthesis of larger amounts of RNA, the yield is often less than desired. The use of the reaction mixture of the present invention results in the yields from such reactions being increased by at least 10 times over the amount obtained with standard reactions.

In vitro transcription reactions are frequently used to synthesize active mRNA for translation experiments. The reaction mixture of the present invention would be particularly useful for this purpose, allowing the production of large amounts of RNA. Normally for mRNA to be translated efficiently it must be capped at the 5' end with a 7-methyl guanosine residue. If desired, a cap analog can be included in the in vitro translation, however, this may reduce the yield of the reaction. Alternatively, uncapped RNA may be synthesized and then translated with a reticulocyte lysate kit, which is supplied with buffers to allow the efficient translation of uncapped mRNAs. Such kits are readily available commercially, and can be purchased from Ambion (2130 Woodward St. #200, Austin, Tex. 78744), for example. It is generally thought that RNA transcripts for use in microinjection experiments should be capped, as this is believed to help protect against nuclease digestion.

The inventors have discovered that the key parameters in polynucleotide synthesis reaction mixtures are (i) relatively high levels of ribonucleotides, (ii) less magnesium than is sufficient to saturate the nucleotides and convert them to the $Mg^{++}$-nucleotide form, (iii) the enzyme inorganic pyrophosphatase, and preferably, (iv) the use of $Mg^{++}$- or Tris-nucleotides. The use of such a reaction mixture results in high yields of RNA in in vitro transcription reactions.

Despite the fact that levels of total nucleotides greater than 8–16 mM are generally thought to inhibit transcription reactions, the inventors have determined that concentrations, of up to 40 mM can be successfully employed when $Mg^{++}$ is present in subsaturating amounts with respect to the total nucleotide concentration. This effect, observed under conditions of subsaturating magnesium, is believed to be due to the inorganic pyrophosphatase cleaving pyrophosphate and making the previously-bound $Mg^{++}$ available to form $Mg^{++}$-NTP substrate complexes. Thus, the actual level of $Mg^{++}$-NTP is low, i.e. in the range which is not inhibitory, but there is an ongoing supply of NTPs available to the reaction when $Mg^{++}$ becomes recycled by the action of the pyrophosphatase and binds previously magnesium-free NTPs. This allows the reaction to continue for a long time at a high rate synthesizing large amounts of product. In any event, whether this model proves to be correct or not, the reaction mixture herein described is nonetheless particularly effective in increasing the yield of polynucleotides in enzymatic synthetic reactions, such as in vitro RNA polymerization.

The following examples illustrate the techniques discovered by the inventors for the creation of a reaction mixture for carrying out the synthesis of polynucleotides. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Use of High Concentrations of Total Nucleotides in in Vitro RNA Sysnthesis

A. Methods

1. Preparation of Template DNA.

Typically the template will consists of a "transcription vector" plasmid containing an insert of interest (for example, a cDNA sequence) cloned into the polylinker region downstream of a bacteriophage promoter, such as a T7, T3, or SP6 promoter. Alternatively, the template DNA may be a PCR-generated DNA fragment, where the phage promoter was incorporated into one of the primers, or even a chemically synthesized oligonucleotide containing the phage promoter (Browning, 1989; Milligan et al., 1987).

Preparation of the template requires pure DNA (preferably CsCl-banded) and restriction enzymes and other reagents that are free of ribonucleases. Most plasmid "miniprep" protocols include a ribonuclease treatment at the later stages to eliminate bacterial RNA. All RNase must be removed before attempting to use the miniprep DNA as template for transcription. This can be done by treating the miniprep with Proteinase K (100–200 $\mu$g/ml) and SDS (0.5%) for 30 minutes-1 hour at 37° C., followed by phenol/$CHCl_3$ extraction and ethanol precipitation. Miniprep DNA prepared in this way is generally an adequate template for transcription, provided the DNA is treated with Proteinase K and then phenol/$CHCl_3$ extracted and ethanol precipitated subsequent to the restriction digestion. The Proteinase K treatment appears to improve the template quality regardless of whether RNase was used in the miniprep procedure.

The DNA is usually digested with a restriction endonuclease to make a template that will generate run-off transcripts of a defined size. To make transcripts of the same sequence as mRNA, the plasmid should be digested with a restriction enzyme that cleaves on the 3' side of the insert (carboxy-terminal end with respect to protein coding). Whilst for mRNA-complementary, "antisense" transcripts, the plasmid should be cleaved on the 5' side (amino terminal end). There are reports that non-specific (i.e. non-promoter dependent) transcription can initiate at 3' protruding ends (Schenborn and Mierendorf, 1985), so it is advisable to use restriction enzymes that leave 5' or blunt ends.

To terminate the restriction digest, one would add a 1/20 volume of 0.5M EDTA, 1/9 volume of 3M sodium acetate, and 2 volumes of ethanol and chill at −20° C. for at least 15 minutes. Then pellet the DNA for 15 minutes by microcentrifugation, remove the supernatent by double aspiration with a drawn-out Pasteur pipet (i.e. after removing the supernatent, re-spin the tube for a few seconds and then remove the residual fluid), and finally resuspend the pellet in $dH_2O$ or TE buffer at a concentration of 0.5 mg/ml. At this stage, it is recommended to check an aliquot of the linearized template on an agarose gel to assess its quality and quantity. Occasionally, restriction enzymes are contaminated with RNase or other inhibitors of transcription; in this case, a Proteinase K/SDS digestion and phenol/chloroform extraction should be done prior to ethanol precipitation.

1 $\mu$g of a 3–5 kb linearized plasmid is generally optimal for a 20 $\mu$l transciption reaction. However, if one wishes to use significantly larger or smaller templates, it may be desirable to increase or decrease the amount of template proportionately. However, the intrinsic transcription efficiently of different templates varies, so if it is desirable to maximize transcriptional efficiency, then the optimal template amount should be determined empiracally.

2. Conducting the Transcription Reaction.

There are seven components of the reaction mixture:

1. Template DNA in water or TE buffer (10 mM Tris pH 8, 1 mM EDTA) at a concentration of 0.5–1 $\mu$g/$\mu$l. The control template is a linearized plasmid containing a 1.7 kb insert under the transcriptional control of the SP6, T7, or T3 promoter, at a concentration of 0.5 $\mu$g/$\mu$l.
2. 10×-concentrated Transcription Buffer containing salts, buffer, dithiothreitol, and other ingredients, optimized for high efficiency transcription. This key component of the reaction mixture varies according to the polymerase enzyme used. See Example III for a complete description.
3. The Ribonucleotide solutions are neutralized buffered solutions of 75 mM (T7 or T3) or 50 mM (SP6) ATP, CTP, GTP, or UTP.
4. Enzyme Mix is a buffered 50% glycerol solution containing 20 U/$\mu$l of SP6, T7, or T3 RNA polymerase, 12.5 U/$\mu$l placental RNase inhibitor, and other components which increase the rate and duration of in vitro transcription reactions (see Example III for a complete description). Placental ribonuclease inhibitor is a non-competitive inhibitor of RNases and is included to inhibit any ribonuclease which may be inadvertantly introduced into the reaction. Note: Oxidation or denaturation of the placental RNase inhibitor can result in the release of active RNase!
5. DNase I (RNase-free) in a 2 U/$\mu$l 50% glycerol solution which can be used to degrade the DNA template at the end of the transcription reaction.
6. Transcription Stop Mix consists of 5M ammonium acetate and 0.25M EDTA. A 1/10 volume of this mixture can be added to the diluted transcription reaction to terminate transcription. It provides sufficient EDTA to chelate divalent cations and to sufficient monovalent cations to allow the RNA to be precipitated after a phenol:chloroform extraction and addition of ethanol.
7. Lithium Chloride Precipitation Solution consists of 7.5M LiCl and 75 mM EDTA. This mixture can be added to the diluted transcription reaction to terminate transcription and precipitate the RNA.

Prior to conducting the reaction, thaw the 10×transcription buffer, the four ribonucleotide solutions and the RNase-free $dH_2O$ from their frozen stocks. Briefly vortex the 10×transcription buffer and ribonucleotide solutions. All reagents should be microfuged briefly before opening to prevent loss and/or contamination of material that may be present around the rim of the tube. Keep the tube of enzyme mix on ice during assembly of the reaction.

The following amounts are for a single 20 $\mu$l reaction. Reactions may be scaled up or down depending on specific requirements, and it should be noted that spermidine in the transcription buffer can lead to precipitation of the template DNA if the reaction is assembled on ice. Add the following amounts of the indicated reagents to a 1.5 ml microfuge tube at room temperature: 2 $\mu$l 10×Transcription Buffer; and 2 $\mu$l ATP solution (75 mM T7 or T3; 50 mM SP6); 2 $\mu$l CTP solution (75 mM T7 or T3; 50 mM SP6); 2 $\mu$l GTP solution (75 mM T7 or T3; 50 mM SP6); 2 $\mu$l UTP solution (75 mM T7 or T3; 50 mM SP6). Or, for convenience, equal volumes of the four ribonucleotide solutions can be mixed together and added as one component instead of adding 2 $\mu$l of each of the four separate ribonucleotide solutions. One may also wish to optionally add 1 $\mu$l of a labeled ribonucleotide to serve as tracer, for example 1 μl, of $^{32}$P-UTP (any specific activity is acceptable). 1 μg of linearized template DNA needs to be added, for example 2 μl of template at a concentration of 0.5 mg/ml, along with 2 μl of enzyme mix; and then RNase-free dH$_2$O is added last to make the final volume up to 20 μl.

Mix the contents by brief gentle vortexing or by gently pipetting the contents up and down a few times, then microfuqe for a few seconds to collect all reaction components at the bottom of the tube. Incubate the tube at 37° C., preferably in a 37° C. incubator (this will eliminate condensation, which may occur if the tube is incubated in a heat block). Incubate for 2–6 hours or longer, depending on the amount of transcript needed and the size and transcriptional efficiency of your template. For the initial reaction with a new template, the recommended incubation time is 4–6 hours. For short transcripts (less than 500 nucleotides), extended incubation times may be advantageous, since more transcription initiation events are required to synthesize a given mass amount of RNA, compared to transcription of longer templates. Thus, with short transcripts, the reaction continues at a significant rate for a longer time period.

To determine the optimum incubation time for maximum yield with a given template, a time-course experiment should be done. In this type of experiment, aliquots of the reaction are removed at various intervals (for example after 2 hours, 4 hours, 6 hours, and overnight incubation) and assessed by TCA precipitation or other means (see below). As a note of caution, whilst the yield may be increased by overnight incubation, RNA degradation is occasionally observed, presumably due to the release of RNase by the placental RNase inhibitor.

After the transcription reaction is complete, the template DNA may be degraded by the addition of 1 μl of RNase-free DNase I and further incubation at 37° C. for 15 minutes. Since the reaction may be viscous due to high RNA concentration, the contents of the tube should be mixed thoroughly after addition of the DNase solution. Note, for many applications it may not be necessary to degrade the template DNA, since it will be present at a very low concentration relative to the RNA.

Before terminating the reaction, one may desire to remove an aliquot to assess the yield. Two alternative methods for recovering RNA from the transcription reaction are recommended. These are phenol/CHCl$_3$ extraction (Method I) and LiCl precipitation (Method II). Phenol/CHCl$_3$ extraction requires slightly more hands-on time, but is a method that is familiar to most people. LiCl precipitation is convenient and effective, but may not be quite as thorough as phenol/CHCl$_3$ for removal of proteins. Also, LiCl does not precipitate transfer RNA and may not precipitate RNA's smaller than 300 nucleotides.

Termination Method 1:phenol/CHCl$_3$ extraction. Stop the reaction by adding 115 μl of RNase-free dH$_2$O and 15 μl of ammonium acetate stop solution and mix thoroughly. Extract the reaction once with an equal volume of water or buffer-saturated phenol/chloroform, and once with an equal volume of chloroform, and optionally, re-extract the organic phase with 50 μl dH$_2$O. Precipitate the RNA by adding 2½ volumes ethanol and mixing well. Chill the reaction for at least 15 minutes at −20° C. Centrifuge for 15 minutes at maximum speed (approx. 12,000 rpm) to pellet the RNA. Carefully remove the supernatent solution and resuspend the RNA in RNase-free dH$_2$O or TE buffer.

For the preparation of RNase-free dH$_2$O: add diethylpyrocarbonate (DEP) to double-distilled, deionized H$_2$O to a concentration of 0.1% (i.e. add 1 ml per liter of H$_2$O), shake well and incubate for several hours, or overnight, at 37° C. or 42° C. Then autoclave for at least 45 minutes, or until the DEP scent is gone.

Termination Method 2: LiCl precipitation. Stop the reaction and precipitate the RNA by adding 30 μl of RNase-free dH$_2$O and 25 μl of lithium chloride precipitation solution and mix thoroughly. Chill the reaction for at least 30 minutes at −20° C. Centrifuge for 15 minutes at maximum speed (approx. 12,000 rpm) to pellet the RNA. Carefully remove the supernatent solution. The pellet can be washed once with 70% ETOH and re-centrifuged to maximize removal of unincorporated nucleotides. It should be noted that the LiCl does not precipitate transfer RNA (tRNA) and may not precipitate RNAs smaller than 300 nucleotides.

3. Determination of Yield of Transcription Products.

The yield of RNA transcripts synthesized can be determined by TCA (trichloroacetic acid) precipitation if a radiolabeled nucleotide tracer (for example, $^{32}$P-UTP) is included in the reaction. After termination of the reaction (or at any time during the reaction), an aliquot (approximately 1 μl) is removed and thoroughly mixed with 100 μl of TE buffer or RNase-free dH$_2$O. Half of the diluted RNA sample is added to a 12×75 mm glass tube containing RNase-free carrier (for example, 50 μg of yeast RNA or sonicated fish sperm DNA) in a volume about 100 μl, mixed, and then 2 ml of 10% TCA is added. The tube is vortexed briefly and placed on ice for 5 minutes. The precipitated nucleic acid is then collected by vacuum filtration through a glass fiber filter that has been wet with TCA. The filter is then rinsed successively with 16% TCA and ethanol. The filter is added to scintillation cocktail and counted. (When using tolulene-based scintillation cocktails, the filter should be dried before counting.) The other half of the diluted RNA is added directly to an aqueous scintillation cocktail and counted. The ratio of the two values is the fraction of labeled nucleotide incorporated into RNA. At a total ribonucleotide concentration of 30 mM (7.5 mM of each of the four NTP's) in a 20 μl reaction, each 1% incorporation corresponds to about 2 μg of RNA synthesized.

The yield can be calculation as follows. In a standard reaction containing a 7.5 mM concentration of each of the four ribonucleotide triphosphates in a 20 μl volume (corresponding to using 2 μl of each of the 4 ribonucleotide solutions), the total amount of NTP's in the reaction is 198 μg (since the sum of the molecular weights of the 4 in an RNA molecule is approximately 1320).

If the TCA precipitation data shows 50% incorporation of a $^{32}$P-UTP tracer, the yield of RNA is 198 μg×50%=99 μg. When assessing yield of RNA by TCA precipitation, it is important to keep in mind that the yield is based on the fraction of label incorporated and the ratio of labeled nucleotide:unlabeled nucleotide (for example, $^{32}$P-UTP: unlabeled UTP). When in vitro transcription reactions are used to make high specific activity probes, the ratio of $^{32}$P-UTP: unlabeled UTP is typically about 1:8 (for example, if 1 μl of 800 Ci/mMole $^{32}$P-UTP at 10 mCi/ml is added to a 20 μl reaction containing a 5 μM concentration of unlabeled UTP). In contrast, in reactions of the present invention containing the same amount of $^{32}$P-UTP but with a 7.5 mM concentration of unlabeled UTP, the ratio of $^{32}$P-UTP: unlabeled UTP is 1:12,000. Therefore, for a given percent incorporation of $^{32}$P-UTP, the yield of RNA is 1500-fold greater in these reactions than in the probe synthesis reaction. (Since the mass amount of $^{32}$P-UTP in the reaction is negligible compared to be mass amount of unlabeled UTP, it can be disregarded in calculating the yield, as in the above example.)

An alternative method for quantitating the RNA synthesized is by ultraviolet light absorption, provided the DNA template and unincorporated nucleotides are first removed. An aliquot of the RNA is diluted and read in a microcuvette at 260 nm and 280 nm. An absorbance of one at 260 nm corresponds to an RNA concentration of 40 µg/ml, and the ratio of the absorbance values at 260 nm and 280 nm should be in the range of 1.8–2.

B. Results

Experiments were conducted to investigate the yield of in vitro RNA transcription reactions using either low (2 mM) or high (18 mM) total nucleotide concentrations. In these experiments, the reaction conditions for the lower level of nucleotides were designed to reflect very typical conditions that are currently in use. A $Mg^{++}$ concentration of 6 mM, i.e. 4 mM greater than the total nucleotide concentration was used. In the higher levels, a total nucleotide concentration of 18 mM was chosen as it was 2 mM greater than any value reported previously in the literature. The experiment was also performed both with, and without added inorganic pyrophosphatase.

Two initial conclusions could be drawn from the results. Firstly, higher nucleotide levels stimulate total synthesis, and secondly, this synthesis is more than two fold greater in the presence of inorganic pyrophosphatase (FIG. 1). At the low nucleotide levels, inorganic pyrophbsphatase was seen to have little effect.

Experiments were then designed to test the hypothesis that high nucleotide concentrations are inhibitory in the presence of excess magnesium and that optimal synthesis would be achieved at high nucleotide and subsaturating magnesium levels. These experiments involved determining the effect of varying the nucleotide concentration in the presence of inorganic pyrophosphatase at three different ratios of magnesium to nucleotides. Each nucleotide concentration was tested with 3 magnesium concentrations, 0.7, 1 or 1.43 times the nucleotide concentration. At 20 mM nucleotides and lower concentrations, the magnesium concentration was found not to be critical. With a 1.43 fold level of magnesium, 30 and 40 mM nucleotides are actually inhibitory relative to 20 mM nucleotides. With equimolar magnesium, nucleotides only become inhibitory above 30 mM. With subsaturating levels of magnesium, nucleotide levels of 40 mM were possible (FIG. 2).

EXAMPLE II

Optimal Salt Concentrations For Use in in Vitro RNA Sysnthesis

The optimal salt levels for transcription reactions were investigated. T7 and T3 polymerases are known to be active in buffers with a $Na^+$ concentration of about 50 mM. However, SP6 polymerase prefers significantly lower salt concentrations, and is believed to operate best in the absence of $Na^+$ (0 mM). Despite this, the nucleotides most likely to be used in in vitro transcription reactions are those that are readliy commercially available, typically $Na^+$, $Li^+$, $K^+$, or $NH_4^+$ (although $Ca^{++}$, $Ba^{++}$ and $Mg^{++}$ nucleotide salts are also available).

The inventors hypothesized that the addition of the very high levels of nucleotides that are contemplated in certain embodiments of the present invention may lead to inhibition by the correspondingly high levels of salt, and particularly, that high $Na^+$ levels may inhibit SP6. For example, adding nucleotides to a total concentration of 20 mM would introduce 45.3 mM of NaCl (Table 2). It was also thought likely that $Ca^{++}$ and $Ba^{++}$ would inhibit polymerase enzymes. Therefore, Tris- and $Mg^{++}$-nucleotides were considered as possible viable alternatives to the commonly available $Na^+$-, $Li^+$-, $K^+$-, $NH_4^+$-nucleotide salts. Since $Mg^{++}$ nucleotides are only available from Sigma in a 95% purity, the inventors did not study these directly.

TABLE 2

Amount of Salt ($Na^{++}$) contributed by di-sodium ATP, CTP, GTP, and trisodium UTP.

| mM final NTP concentration nucleotides | $Na^+$ concentration due to |
|---|---|
| 2 mM NTPs | 4.5 mM |
| 10 | 22.7 mM |
| 20 | 45.3 mM |
| 30 | 68.0 mM |

The effect of adding NaCl to an SP6 polymerase transcription reaction using 2 mM total nucleotides, and thus only 4.5 mM of $Na^+$, was investigated (FIG. 3). Extrapolating between the 40 and 60 mM NaCl points indicates that 45.3 mM $Na^+$ would inhibit the reaction by about 50%. Using Tris-nucleotides (Sigma Cat. #A-0270, C-1756, G-6131, U-8378) was found to result in higher yields of RNA synthesized. This effect was especially apparent with SP6 polymerase, but was also seen with T7 polymerase. In SP6 transcription experiments using 20 mM total nucleotides, the use of Tris nucleotides resulted in almost 14 times more RNA synthesized than with the sodium nucleotides (Table 3). With T7 polymerase a combination of five parts sodium nucleotides and one part Tris nucleotides resulted in over twice the amount of RNA synthesized with just sodium nucleotides. The sodium coming in with the mixture of Tris and sodium nucleotides was 56.6 mM and with sodium nucleotides was 68 mM. Thus, higher concentrations of nucleotides can be used if Tris, or a counter ion other than $Na^+$, $K^+$ or $NH_4^+$ is used. It is thought to be highly likely that the use of Tris nuceotides, inorganic pyrophosphatase and subsaturating magnesium levels will allow even higher (>30 mM) nucleotide concentrations to be used, resulting in even greater yields.

TABLE 3

Effect of Tris-nucleotides on In Vitro Transcription yields with SP6 RNA polymerase and T7 RNA polymerase

| | | µg RNA synthesis at 6 hours |
|---|---|---|
| A. | SP6 RNA polymerase | |
| | 20 mM NTPS | 1.99 µg |
| | 20 mM Tris-NTPs | 27.7 µg |
| B. | T7 RNA polymerase | |
| | 30 mM NTPs | 10.36 µg |
| | 25 mM NTPS + 5 mM Tris-NTPS | 23.4 µg |

1. T7 Reactions were carried out similarly to as described in FIGS. 1 and 2. SP6 reactions were carried out as described in FIG. 3 except that the amount of SP6 polymerase was 2000 U/ml, pyrophosphatase was 15 U/ml and human placental ribonuclease inhibitor was present at 1250 U/ml. The reactions were incubated at 37° C. for 6 hours.

The reaction mixture of the present invention was then compared to the most effective reaction conditions that have been sorted in the literature (Cunningham & Ofengand, 1990). However, comparisons between different laboratories are difficult, partly because of the different templates used.

In this comparison, set forth in Table 4 below, use of the reaction conditions described herein resulted in a yield of transcription product that was 2.85 fold greater than was obtained using the reaction conditions described by Cunningham & Ofengand (1990). Note that in Table 4, sample 1 was carried out in accordance with the present invention, whereas samples 2 through 5 were carried out in accordance with the conditions described by Cunningham & Ofengand.

TABLE 4

Comparison of Cunningham and Ofengand (1990) reaction conditions with current best mode conditions.

| Sample | NTP mM | $Ma^{++}$ mM | PPase Units/ml | RNA yield (µg) |
|---|---|---|---|---|
| 1 | 30 | 20 | 15 | 107 |
| 2 | 10 | 8 | 0 | 14.5 |
| 3 | 10 | 8 | 15 | 37.5 |
| 4 | 10 | 18 | 0 | 27.8 |
| 5 | 10 | 18 | 15 | 36.7 |

Each reaction contained 50 µg/ml linearized template DNA (Xef1 template), $2 \times 10^3$ U/ml T7 RNA polymerase, 1250 U/ml human placental ribonuclease inhibitor and the indicated amounts of nucleotides, $Mg^{++}$, and yeast inorganic pyrophosphatase where indicated. The buffer was 40 mM Tris-HCl (pH 8.0), 2 mM spermidine and 10 mM DTT. The reaction volume was 20 µl and was incubated for 6 hours at 37° C. At 6 hours a 1 µl aliquot was removed and diluted into 400 µl of 1 mg/ml salmon sperm DNA and total cpm and acid precipitable cpm were determined.

EXAMPLE III

Components of Reaction Mixtures for Optimal in Vitro RNA Sysnthesis

From a consideration of the results of several experiments, such as described above, optimal conditions were developed for conducting in vitro RNA transcription reactions. The optimal conditions vary depending on the RNA polymerase enzyme used.

T7/T3 Reaction Conditions

The following components should be mixed in the indicated order at room temperature:

| | |
|---|---|
| 2 µl of | 10x reaction buffer: |
| | 400 mM Tris-HCl pH 8.0 (USB) |
| | 100 mM DTT |
| | 20 mM Spermidine-HCl (Sigma) |
| | 200 mM $MgCl_2$ |
| 6 µl of | Nucleotide mix: |
| | 25 mM of each ribonucleotide (A, C, G, U) Nucleotides were neutralized with NaOH. (Boehringer/Mannheim, Cat. #519987, 414581, 103843, 110221) |
| 2 µl of | Enzyme mix: |
| | 12.5 U/µl human placental ribonuclease inhibitor (Ambion) |
| | 20 U/µl T7/T3 RNA polymerase (Ambion) |
| | 0.15 U/µl yeast inorganic pyrophosphatase (Sigma) |
| 2 µl of | 0.5 µg/µl Xef1 linearized template DNA $^{32}$p-nucleotide for tracer if desired |
| µl of | $H_2O$ (or, as required, to a final volume of 20 µl) |

8P6 Reaction Conditions

The following ingredients should be mixed together in the indicated order at room temperature:

| | |
|---|---|
| 2 µl of | 10x reaction buffer: |
| | 400 mM Tris-HCl pH 8.0 |
| | 100 mM DTT |
| | 20 mM Spermidine |
| | 90 mM $MgCl_2$ |
| 4 µl of | Nucleotide mix: |
| | 25 mM Tris form of each ribonucleotide (A, C, G, U) Nucleotides were neutralized with NaOH. (Sigma Cat. #A-0270, C-1756, G-6131, U-8378) |
| 2 µl of | Enzyme mix: |
| | 12.5 U/µl human placental ribonuclease inhibitor (Ambion) |
| | 20 U/µl SP6 RNA Polymerase (Ambion) |
| | 0.15 U of yeast inorganic pyrophosphatase (Sigma) |
| 2 µl of | 0.5 µg/µl Xef1 linearized template DNA $^{32}$P-nucleotide for tracer if desired |
| 10 µl of | $H_2O$ (or, as required, to a final volume of 20 µl) |

Using the above two reaction mixtures, the RNA transcription reactions were incubated at 37° C. for 2–6 hours. It was determined that the reaction was 65% complete at 2 hours, 90% complete at 4 hours, and that the reaction had reached completion at 6 hours. To quantify the amount of RNA synthesized, 10 µCi of $\alpha$-$^{32}$P-UTP (800 Ci/mmole) was added to the reaction. At various time points 1–2 µl of the reaction was diluted into 400 µl of 1.0 mg/ml Salmon Sperm DNA. An aliquot of 100 µl was assayed for total cpm and another 100 µl aliquot was acid precipitated. The ratio of these two values (percentage incorporation) was multiplied by the mass of nucleotide present to determine the mass of RNA synthesized. In the first case (7.5 mM of each nucleotide), the mass of nucleotides present was 198 µg; and in the second case (5.0 mM of each nucleotide), it was 132 µg.

EXAMPLE IV

Use of High Nucleotide Reaction Mixtures in Other Polynucleotide Synthetic Reactions 1. Synthesis of Capped RNA Transcripts Most mRNA molecules have a 5' 7 methyl guanosine residue or cap which functions both in the protein synthesis initiation process and also serves to protect the mRNA from nuclease digestion intracellular. Capped in vitro transcripts can be synthesized by adding cap analog directly to the transcription reaction. It is frequently not necessary to cap in vitro transcripts for in vitro translation experiments. The yield of in vitro translation experiments with uncapped in vitro transcripts can equal that of capped transcripts by increasing the amount of uncapped transcript added to the translation reaction and decreasing the $K^+$ concentration.

In vitro transcripts which are to be microinjected into oocytes or other cells, or for transfection experiments or in vitro splicing reactions, should be capped. Accordingly, one would wish to cap any transcripts made using the present reaction medium before conducting these experiments.

However, there are several factors which should be considered. These are that cap analog is a relatively expensive reagent, that reactions which contain cap analog have significantly lower yields, and that unincorporated cap analog is a potent inhibitor of protein synthesis initiation (Kreig & Melton, 1987).

The standard strategy to synthesize capped transcripts is to reduce the level of GTP to 1/10 the normal concentration and replace this with cap analog. This results in a high proportion of the transcripts being capped. Unfortunately it also significantly decreases the yield of the transcription reaction often to 20% or lower. To conserve cap analog and increase the efficiency of the transcription reaction, many workers have been decreasing the ratio of cap analog to GTP. Four to one cap:GTP is frequently used, although 1:1 has also been used. It is likely, however, that the fraction of capped mRNA molecules decreases as the ratio of cap to GTP decreases. Thus, depending on the specific requirements, the inventors contemplate that a four to one ratio of cap analog to GTP be used in these embodiments, unless it is essential that almost all of the transcripts be capped. The concentration of GTP in SP6 polymerase reactions is normally 5 mM and for T7 and T3 polymerases, it is 7.5 mM. The nucleotide stocks proposed to be of use for SP6 are 50 mM and for T7 and T3, 75 mM. Thus, it is recommended that a portion of the GTP stock should be mixed with 4 parts water and 2 µl of the 1:4 diluted GTP added to a 20 µl reaction. 2 µl of a 40 mM stock of cap analog should be added to a 20 µl SP6 reaction and 3 µl for 20 µl T7 or T3 reactions. The remainder of the reaction should be assembled as usual.

2. Transcription of PCR Products Containing Phage Promoters

By using primers which flank the phage promoter(s) in the transcription vector, an inserted DNA fragment can be amplified and used directly as the template using the reaction mixture of the present invention. Alternatively, the phage promoter sequence can be appended to one of the PCR primers and incorporated into the PCR product. Often the amplified DNA can be used directly in the transcription reaction with no purification after the PCR. Typically, 5 µl of a 100 µl PCR, corresponding to about 0.5 µg of double-stranded DNA, is used as a template in the reaction. However, if the yield of RNA is low, it may be necessary to purify the amplified DNA before use to remove inhibitors, for example, by one of the procedures that use binding to and elution from glass particles, or by phenol/chloroform extraction and ethanol precipitation.

3. Reactions involving DNA Polymerases

The inventors predict that the strategy of employing high nucleotide concentrations, less than saturating Mg concentrations and the enzyme inorganic pyrophosphatase will also prove to be beneficial in reactions employing DNA polymerase. Two obvious areas for improvement would be the amplification technologies of PCR (polymerase chain reaction) and 3SR (Self-sustained Sequence Replication).

PCR reactions typically have all 4 deoxynucleotides present at a concentration of 0.2 mM each (0.05–0.20 mM), and $Mg^{++}$ is typically added at 1.5 mM; leaving a free $Mg^{++}$ concentration of about 0.7 mM. Currently, an increase in the nucleotide concentrations is known to lead to increased error rates (Erlich, 1989).

3SR reactions utilize conditions similar to those used for in vitro transcription reactions, except that they also have deoxynucleotide triphosphates and the enzyme reverse transcriptase. Amplification involves both DNA and RNA polymerase activities. One protocol for this procedure utilizes total ribonucleotide concentrations of 24 mM and deoxyribonucleotide concentrations of 4 mM and $Mg^{++}$ at 30 mM, resulting in a small free $Mg^{++}$ excess. In addition, the optima for monovalent salts ($K^+$, 20 mM; $Na^+$ 25 mM) is known to be quite low (Fahy et al., 1991). The inventors propose that the strategy disclosed herein of using high nucleotide concentrations, less than saturating $Mg^{++}$, inorganic pyrophosphatase and Tris nucleotides will benefit 3SR reactions, both by increasing yields, and possibly by decreasing error rates.

The investigation of the use of the present reaction mixture in 3SR reactions is straightforward. Several reactions which contained different increased levels of Tris ribonucleotides (28, 32, 36, 40, 44, 48 mM) would be set up, and the $Mg^{++}$ levels optimized by limited experimentation. $Mg^{++}$ levels would start at a level equal to the total nucleotide concentration +5 mM, and would decrease at 2.5 mM intervals. These experiments would be performed in the presence of 15 units/ml of inorganic pyrophosphatase. Once elevated ribonucleotide and $Mg^{++}$ optima had been determined, the optimal level for inorganic pyrophosphatase would be determined. At this point, the effect of increasing deoxynucleotide levels would be determined (4, 6, 8, 10, 12 mM). At each of these different deoxynucleotide levels the $Mg^{++}$ optima would be determined.

To test the use of higher nucleotide reaction mixtures in PCR reactions it will be necessary to use a thermostable inorganic pyrophosphatase. Such thermostable enzymes may be obtained from a thermophilic bacteria. The inventors suggest that purification of inorganic pyrophosphatase from *Thermus aquaticus*, using methods based on those described by Verhoevern et al., (1986), will probably be most appropriate.

The effect on PCR reactions of increasing the concentration of nucleotides and subsaturating levels of $Mg^{++}$, in the presence of thermostable inorganic pyrophosphatase will be systematically investigated, assessing both the yield and error frequency in these experiments. Indeed, a critical feature of PCR is the error frequency, which can be quite high. In a recent preliminary report, it was stated that $Mg^{++}$ and nucleotide concentrations were variables that affected both error rates and yields in PCR reactions (Ling et al., 1991). The inventors contemplate that significantly more beneficial reslts may be obtained by using high nucleotide reaction mixtures in which the nucleotides are in a form other than as a salt with $Na^+$, $Li^+$, $K^+$, $Ba^{++}$, or $NH_4^+$, such as a $Mg^{++}$ or Tris-nucleotide.

4. DNA and RNA Ligase Reactions

The enzymes T4 DNA and RNA ligase both require ATP for ligation reactions which is cleaved to release AMP and pyrophosphate. Typical levels of ATP in ligation reactions currently range from 0.5 to 5 mM. The higher levels of ATP can lead to problems such as the formation of reaction product which has been modified by the addition of 5' AMP to the ligated molecule (Hinton et al., 1982). The inventors propose that the addition of pyrophosphatase to the reaction mixture along with high ATP and low $Mg^{++}$ levels may lead to increases in yield and/or reaction rates. This would be examined by conducting ligase reactions in which increasing ATP concentrations were used along with subsaturating levels of $Mg^{++}$ in the presence of pyrophosphatase.

EXAMPLE V

MEGAscript™ in Vitro RNA Transcription Kit Manual

The following is the manual supplied by Ambion with its MEGAscript™ in vitro RNA transcription kits:

I. Introduction

Ambion's MEGAscript kits are designed to give very high yields of in vitro transcription reactions.

MEGAscript kits contain nucleotides, reaction buffer, enzyme mix including placental ribonuclease inhibitor and RNA polymerase, RNase-free DNase, reagents for recovery of RNA, a control transcription template and a comprehensive instruction manual.[1] The kits contains sufficient reagents to perform forty 20 µl reactions which, when used with the control template supplied with the kit, will yield at least 4–5 mg of RNA.

Some components of the three MEGAscript kits (SP6, T7, and T3) differ between the kits. The lox transcription buffer, control template, enzyme mix, and ribonucleotide solutions should not be interchanged between different versions of the MEGAscript kit.

The RNA polymerases from SP6, T7, and T3 bacteriophages are widely used for the in vitro synthesis of RNA transcripts from DNA templates cloned into plasmid vectors which contain the corresponding SP6, T7, or T3 promoters. By digesting the template with a restriction enzyme that cleaves distal to the phage promoter, a "run-off" transcript of a defined size can be synthesized. The SP6, T7, and T3 RNA polymerases have a high specificity for their respective 23 bp promoters. Most modern multi-purpose cloning vectors contain two different opposing phage promoters flanking a multiple cloning site. The high promoter specificity of the RNA polymerases allows transcription of one strand of the template with virtually no transcription from the promoter on the opposite strand.

In vitro transcription reactions are typically used for two distinct purposes. The first is the synthesis of high specific activity RNA probes. For these reactions the concentration of the labeled nucleotide used, for example $^{32}$P-CTP or $^{32}$P-UTP, is very low (on the order of 3–10 µM). Ambion offers 5 different in vitro transcription kits for this purpose (MAXIscript™ kits SP6, T7, T3, SP6/T7, and T7/T3). The second purpose is the synthesis of larger amounts of unlabeled or low specific activity RNA for a variety of uses such as mRNA for in vitro translation reactions, antisense/microinjection studies, to drive hybridization reactions for the construction of subtractive cDNA libraries, etc. In large-scale transcription reactions the concentration of all 4 nucleotides is high, well above the $K_m$ for the enzyme. While conventional transcription reactions (e.g. the MAXIscript kit) can be used for this purpose, Ambion's new MEGAscript kits typically yield over 10 times the amount of transcription products as standard reactions. MEGAscript kits are not recommended for synthesis of high specific activity probes. (Krieg and Melton, 1987) In vitro transcription reactions are frequently used to synthesize active mRNA for translation experiments. Normally for mRNA to be translated efficiently it must be capped at the 5' end with a 7-methyl guanosine residue. MEGAscript kits are ideal for this purpose (cap analog is not included in the kit). However, the use of cap analog in any transcription reaction greatly reduces the yield of the reaction. (ref) An alternative is to synthesize uncapped RNA and then translate it with Ambion's Retic Lysate IVT kit, which is supplied with buffers that allow the efficient translation of uncapped mRNAs. Transcripts for microinjection experiments should be capped since this helps protect them from nuclease digestion.

A. Storage and Stability

The kit should be stored at −20° C. in a non-frost-free freezer. The reagents are stable for at least 6 months from the time the kit is shipped.

B. Materials Provided with the Kit (40 Reactions)

| | | |
|---|---|---|
| 1. | 100 µl | Optimized 10x Transcription Buffer |
| 2. | 90 µl | ATP Solution (75 mM T7 or T3, 50 mM SP6) |
| 3. | 90 µl | CTP Solution (75 mM T7 or T3, 50 mM SP6) |
| 4. | 90 µl | GTP Solution (75 mM T7 or T3, 50 mM SP6) |
| 5. | 90 µl | UTP Solution (75 mM T7 or T3, 50 mM SP6) |
| 6. | 90 µl | Enzyme Mix: a combination of 0.5 u/µl Placental Ribonuclease Inhibitor, 20 u/µl bacteriophage SP6, T7, or T3 RNA polymerase (see note below), and other components required for optimum RNA synthesis. Supplied in 50% glycerol buffer. |
| 7. | 45 µl | RNase-free DNase I (2 units/µl). Supplied in 50% glycerol buffer. |
| 8. | 10 µl | linearized DNA control template pXef-1: 0.5 mg/ml solution of a plasmid with a 1.7 kb insert containing the Xenopus elongation factor I gene, under the transcriptional control of the SP6, T7 or T3 bacteriophage promoter (see note below). |
| 9. | 1 ml | Ammonium Acetate Stop Solution: 5 M Ammonium Acetate, 250 mM EDTA. |
| 10. | 1.4 ml | Lithium Chloride Precipitation Solution: 7.5 M Lithium Chloride, 75 mM EDTA. |
| 11. | 1 ml | RNase-free distilled deionized $H_2O$ |

C. Materials Not Provided With Kit

1. DNA template in suitable transcription vector.
   Suggested concentration 0.5 mg/ml in $dH_2O$ or TE buffer.
2. RNase-free $dH_2O$ for dilution of reaction following transcription.
3. (optional) Labeled nucleotide, for example $^{32}$P-UTP or $^{32}$P-CTP, for inclusion in the reaction as a tracer to aid in the quantitation and assessment of the RNA synthesized. Any specific activity is acceptable.
4. (optional) 7-methyl guanosine, for synthesizing capped transcripts
5. (optional) For purification of RNA following transcription:
   a. buffer or water-saturated phenol/chloroform
   b. high grade ethanol

D. Related Products Available From Ambion

1. Retiv Lysate IVT™ in vitro translation kit (Cat. #1200), with buffers optimized for translating both capped and uncapped transcripts.
2. Wheat Germ IVT™ in vitro translation kit (Cat. #1250)
3. pSP6/β-actin control template DNA (Cat. #7315)
4. Multipurpose cloning/transcription vectors pT3 T7 19U (Cat. #6020) and pT3 T7 18U (Cat. #6020).
5. Placental Ribonuclease Inhibitor (Cat. #2682)
6. RNase-free DNase I (Cat. #2222)
7. Proteinase K (Cat. #2542)

Note: The MEGAscript kit contains reagents sufficient for 40 reactions, including at least 10% extra to allow for pipetting losses.

II. Experienced Users Protocol For Large-Scale RNA Sysnthesis

A. Preparation of Template

For synthesis of run-off transcripts of defined size, the double-strand DNA template should be digested to completion with a suitable restriction enzyme that cleaves distal to the promoter. It is preferable to use enzymes which cleave the DNA leaving either a 5' overhang or blunt ends. A low level of transcription from 3' overhanging ends (produced by Kpn I, Pst I, etc.) has been observed (Schenborn and Mierindorf, 1985). After restriction enzyme digestion, the template may be purified by phenol/chloroform extraction and ethanol precipitation according to standard procedures, and dissolved in water or TE buffer at a convenient concentration, for example, 0.5 mg/ml. In general, any DNA which is of sufficient purity to be easily digested with restriction enzymes can be used for in vitro transcription. However, the highest transcription efficiency is seen with CsCl purified DNA.

B. Assembly of the Transcription Reaction (Note: for synthesizing capped transcripts, please refer to Section IV-B)

1. Thaw the 10×Transcription Buffer, four Ribonucleotide Solutions and RNase-free dH$_2$O. Briefly vortex the 10×Transcription Buffer and Ribonucleotide Solutions. All reagents should be microfuged briefly before opening to prevent loss and/or contamination of material that may be present around the rim of the tube. Keep the tube of Enzyme Mix on ice during assembly of the reaction.
2. Add the following amounts of the indicated reagents in the order shown to a 1.5 ml microfuge tube at room temperature:

Note: Spermidine in the trascription buffer can lead tpprecipitation of the template DNA if the reaction is assembled on ice.

a. RNase-free dH$_2$O to make a final volume of 20 μl after all other components are added b. 2 μl 10×Transcription Buffer c. 2 μl ATP solution* (75 mM T7 or T3; 50 mM SP6)

d. 2 μl CTP solution* (75 mM T7 or T3; 50 mM SP6)

e. 2 μl GTP solution* (75 mM T7 or T3; 50 mM SP6)

f. 2 μl UTP solution* (75 mM T7 or T3; 50 mM SP6)

g. 1 μl (optional) labeled ribonucleotide to serve as tracer, for example 1 μl of $^{32}$P-UTP (any specific activity is acceptable)

h. 1 μg linearized template DNA, for example 2 μl of template at concentration of 0.5 mg/ml i. 2 μl Enzyme Mix Mix contents by brief gentle vortexing or mixing with a pipettor and then microfuge tube briefly to collect all the reaction mixture at the bottom of the tube.

Note: For convenience, equal volumes of the four ribonucleotide solutions can be mixed together and added as one component instead of adding 2 μl of each of the four separate ribonucleotide solutions. An empty labeled tube is provided for this purpose.

C. Incubate the reaction at 37°, preferably in a 37° cabinet incubator. (This will prevent condensation, which may occur if the tube is incubated in a heat block.) The incubation time will typically be between 2 and 6 hours, depending on the size and intrinsic transcription efficiency of the template. See Section III-C for further discussion of incubation time.

D. To Remove the DNA Template, add 1 μl of RNase-free DNase I to the Reaction, Mix Thoroughly, Microfuge Momentarily, and Incubate at 37° for 15 min.

Note: For many applications it may not be necessary to degrade the template.

E. Two Alternative Procedures are Given for Terminating the Reaction and Recovering the RNA.

Method 1.

Stop the reaction by adding 115 μl of RNase-free dH$_2$O (not supplied with the kit) and 15 μl of Ammonium Acetate Stop Solution and mixing thoroughly. Extract the reaction once with an equal volume of water or buffer-saturated phenol/chloroform, and once with an equal volume of chloroform. Optional; re-extract the-organic phase with 50 μl dH$_2$O. Precipitate the RNA by adding 2½ volumes ethanol and mixing well. Chill the reaction for at least 15 minutes at −20°. Centrifuge for 15 minutes at maximum speed to pellet the RNA. Carefully remove the supernatent solution and resuspend the RNA in RNase-free dH$_2$O or TE buffer. See (Appendix for preparation of RNase-free dH2O.)

Method 2.

Stop the reaction and precipitate the RNA by adding 30 μl of RNase-free dH$_2$O (not supplied with the kit) and 25 μl of Lithium Chloride Precipitation Solution. (Appendix for preparation of RNase-free dH$_2$O.) Mix thoroughly. Chill the reaction for at least 30 minutes at −20°. Centrifuge for 15 minutes at maximum speed to pellet the RNA. Carefully remove the supernatent solution. The pellet can be washed once with 70% ETOH and re-centrifuged to maximize removal of unincorporated nucleotides.

Note: LiCl does not precipitate transfer RNA and may not precipitate RNAs smaller than 300 nucleotides.

III. New Users Protocols

A. Preparation of Template DNA

Typically the template consists of a "transcription vector" plasmid containing an insert of interest (for example, a cDNA sequence) cloned into the polylinker region downstream of a bacteriophage (T7, T3, or SP6) promoter. (Alternatively, the template DNA may be a PCR-generated DNA fragment, where the phage promoter was incorporated into one of the primers or a chemically synthesized oligonucleotide containing the phage promoter.) (Browning, 1989; Milligan et al., 1987) Preparation of.the template is relatively straightforward, requiring clean DNA (preferably CsCl-banded) and restriction enzymes and other reagents that are free of ribonucleases. Most plasmid "miniprep" protocols include a ribonuclease treatment at the later stages to eliminate bacterial RNA. All RNase must be removed before attempting to use the miniprep DNA as template for transcription. This can be done by treating the miniprep with Proteinase K (100–200 μg/ml) and SDS (0.5%) for 30 minutes-1 hour at 37°, followed by phenol/CHCl$_3$ extraction and ethanol precipitation. We find that miniprep DNA generally (but not always) is an adequate template for transcription, provided the DNA is treated with Proteinase K and then phenol/CHCl$_3$ extracted and ethanol precipitated subsequent to the restriction digestion. The Proteinase K treatment appears to improve the template quality regardless of whether RNase was used in the miniprep procedure.

The DNA is usually digested with a restriction endonuclease to make a template that will generate run-off transcripts of a defined size. To make transcripts of the same sequence as mRNA, the plasmid should be digested with a restriction enzyme that cleaves on the 3' side of the insert (carboxy-terminal end with respect to protein coding), while for mRNA-complementary "antisense" transcripts the plasmid should be cleaved on the 5' side (amino terminal end). There are reports that non-specific (i.e. non-promoter dependent) transcription can initiate at 3' protruding ends (Schenborn and Mierendorf, 1985), so it is advisable to use restriction enzymes that leave 5' or blunt ends. Routinely, we terminate the restriction digest by adding a 1/20 volume of 0.5 M EDTA, 1/9 volume of 3 M sodium acetate, and 2 volumes of ethanol, chilling at −20° for at least 15 min., pelleting the DNA for 15 min. in a microcentrifuge, removing the supernatent by double aspiration with a drawn-out Pasteur pipet (i.e. after removing the supernatent, re-spin the tube for a few seconds and then remove the residual fluid), and finally resuspending the pellet in dH$_2$O or TE buffer at a concentration of 0.5 mg/ml. It is a good idea to check an aliquot of the linearized template on an agarose gel to assess its quality and quantity. Occasionally, restriction enzymes are contaminated with RNase or other inhibitors of transcription; in this case, a Proteinase K/SDS digestion and phenol/chloroform extraction should be done prior to ethanol precipitation.

1 μg of a 3–5 kb linearized plasmid is generally optimal for a 20 μl transciption reaction. However, if your template is significantly larger or smaller, it may be desirable to increase or decrease the amount of template proportionately. The intrinsic transcription efficiently, however, of templates differs, so if it is desirable to maximize transcriptional efficiency, then the optimal template amount should be determined empirically.

B. Components of the MEGAscript Kit

1. Template DNA in water or TE buffer (10 mM Tris pH 8, 1 mM EDTA) at a concentration of 0.5–1 μg/μl. The control template is a linearized plasmid containing a 1.7 kb insert under the transcriptional control of the SP6, T7, or T3 promoter, at a concentration of 0.5 μg/μl.
2. 10×-concentrated Transcription Buffer containing salts, buffer, dithiothreitol, and other ingredients, optimized for high efficiency transcription.
3. The Ribonucleotide solutions are neutralized buffered solutions of 75 mM (T7 or T3) or 50 mM (SP6) ATP, CTP, GTP, or UTP.
4. Enzyme Mix is a buffered 50% glycerol solution containing 20 u/μl of SP6, T7, or T3 RNA polymerase, 0.5 u/μl placental RNase inhibitor, and other components which increase the rate and duration of in vitro transcription reactions. Placental ribonuclease inhibitor is a non-competitive inhibitor of RNases and is included to inhibit any ribonuclease which may be inadvertently introduced into the reaction.

Note: Oxidation or denaturation of the placental RNase inhibitor can result in the release of active RNase!

5. DNase I (RNase-free) is supplied as a 2 u/μl 50% glycerol solution which can be used to degrade the DNA template at the end of the transcription reaction.
6. Transcription Stop Mix consists of 5 M ammonium acetate and 0.25 M EDTA. A 1/10 volume of this mixture can be added to the diluted transcription reaction to terminate transcription. It provides sufficient EDTA to chelate divalent cations and to sufficient monovalent cations to allow the RNA to be precipitated after a phenol:chloroform extraction and addition of ethanol.
7. Lithium Chloride Precipitation Solution consists of 7.5 M LiCl and 75 mM EDTA. This mixture can be added to the diluted transcription reaction to terminate transcription and precipitate the RNA.

C. Assembly of the Transcription Reaction

Thaw the 10×Transcription Buffer, four Ribonucleotide Solutions and RNase-free dH$_2$O. Briefly vortex the 10 + Transcription Buffer and Ribonucleotide Solutions. All reagents should be microfuged briefly before opening to prevent loss and/or contamination of material that may be present around the rim of the tube. Keep the tube of Enzyme Mix on ice during assembly of the reaction. The following amounts are for a single 20 μl reaction. Reactions may be scaled up or down depending on specific requirements.

Add the following amounts of the indicated reagents to a 1.5 ml microfuge tube at room temperature:

Note: Spermidine in the transcription buffer can lead to precipitation of the template DNA if the reaction is assembled on ice.

1. RNase-free dH$_2$O to make a final volume of 20 μl after all other components are added
2. 2 μl 10×Transcription Buffer
3. 2 μl ATP solution* (75 mM T7 or T3; 50 mM SP6)
4. 2 μl CTP solution* (75 mM T7 or T3; 50 mM SP6)
5. 2 μl GTP solution* (75 mM T7 or T3; 50 mM SP6)
6. 2 μl UTP solution* (75 mM T7 or T3; 50 mM SP6)
7. 1 μl (optional) of labeled ribonucleotide to serve as tracer, for example 1 μl of $^{32}$P-UTP (any specific activity is acceptable)
8. 1 μg of linearized template DNA, for example 2 μl of template at concentration of 0.5 mg/ml
9. 2 μl Enzyme Mix Note: For convenience, equal volumes of the four ribonucleotide solutions can be mixed together and added as one component instead of adding 2 μl of each of the four separate ribonucleotide solutions. An empty labeled tube is provided for this purpose.

Mix contents by brief gentle vortexing or by gently pipetting the contents up and down a few times, then microfuge for a few seconds to collect all reaction components at the bottom of the tube. Incubate the tube at 37°, preferably in a 37° incubator (this will eliminate condensation, which may occur if the tube is incubated in a heat block). Incubate for 2–6 hours or longer, depending on the amount of transcript needed and the size and transcription efficiency of your template. For the initial reaction with a new template, the recommended incubation time is 4–6 hours. For short transcripts (less than 500 nt), extended incubation times may be advantageous, since more transcription initiation events are required to synthesize a given mass amount of RNA, compared to transcription of longer templates. Thus, with short transcripts, the reaction continues at a significant rate for a longer time period. To determine the optimum incubation time for maximum yield with a given template, a time-course experiment should be done. In this type of experiment, aliquots of the reaction are removed at various intervals (for example after 2 hours, 4 hours, 6 hours, and overnight incubation) and assessed by TCA precipitation or other means (see Section IV-A).

Note of Caution: While the yield may be increased by overnight incubation, we occasionally observe RNA degradation, presumably due to the release of RNase by the placental RNase inhibitor.

D. Removal of DNA Template

After the transcription reaction is complete, the template DNA may be degraded by the addition of 1 μl of RNase-free DNase I and further incubation at 37° for 15 min. Since the reaction may be viscous due to high RNA concentration, the contents of the tube should be mixed thoroughly after addition of the DNase solution. Note, for many applications it may not be necessary to degrade the template DNA, since it will be present at a very low concentration relative to the RNA.

E. Termination of the Reaction

Before terminating the reaction, you may want to remove an aliquot to assess the yield (see Section IV-A). We provide two alternative methods for recovering RNA from the transcription reaction. These are phenol/CHCl$_3$ extraction (Method I) and LiCl precipitation (Method II). Phenol/CHCl$_3$ extraction requires slightly more hands-on time, but is a method that is familiar to most people. LiCl precipitation is convenient and effective, but may not be quite as thorough as phenol/CHCl$_3$ for removal of proteins. Also, LiCl does not precipitate transfer RNA and may not precipitate RNA's smaller than 300 nucleotides.

Method 1.

Stop the reaction by adding 115 μl of RNase-free dH$_2$O (not supplied with the kit) and 15 μl of Ammonium Acetate Stop Solution and mixing thoroughly. Extract the reaction once with an equal volume of water or buffer-saturated phenol/chloroform, and once with an equal volume of chloroform optional; re-extract the organic phase with 50 μl dH$_2$O. Precipitate the RNA by adding 2½ volumes ethanol and mixing well. Chill the reaction for at least 15 minutes at −20°. Centrifuge for 15 minutes at maximum speed to pellet the RNA. Carefully remove the supernatent solution and resuspend the RNA in RNase-free dH$_2$O or TE buffer. See (Appendix for preparation of RNase-free dH$_2$O)

Method 2.

Stop the reaction and precipitate the RNA by adding 30 µl of RNase-free dH$_2$O (not supplied with the kit) and 25 µl of Lithium Chloride Precipitation Solution. (Appendix for preparation of RNase-free dH$_2$O) Mix thoroughly. Chill the reaction for at least 30 minutes at −20°. Centrifuge for 15 minutes at maximum speed to pellet the RNA. Carefully remove the supernatent solution. The pellet can be washed once with 70% ETOH and re-centrifuged to maximize removal of unincorporated nucleotides.

Note: LiCl does not precipitate transfer RNA and may not precipitate RNAs smaller than 300 nucleotides.

IV. Additional Procedures

A. Analysis of Transcription Products by Gel Electrophoresis

The size of the RNA can be assessed by running an aliquot of the reaction on an agarose or polyacrylamide gel. Transcripts larger than about 1.5 Kb should be run on agarose gels, while polyacrylamide gels (4–5%) may be used for sizing smaller transcripts. Since secondary structure in the transcript may result in aberrant migration and/or the presence of multiple bands, the gel should be run under denaturing conditions. For agarose gels, this means glyoxal or formaldehyde gels should be prepared and run according to standard procedures (ref). RNA run on agaros or polyacrylamide gels may be visualized by subsequently staining the gel with ethidium bromide. (Note, because single-stranded nucleic acid does not bind ethidium as efficiently as does double-stranded, the fluorescence of RNA samples on a denaturing agarose gel will be much less than for the same amount of RNA, which assumes a conformation having substantial secondary structure, run on a native gel.)

If the transcription reaction contained a tracer amount of label (for example $^{32}$P-UTP), the RNA can be visualized by autoradiography. Agarose gels should be dried before exposing to X-ray film, while thin (0.75 mm thick) polyacrylamide gels may be transferred to chromatography paper, covered with plastic wrap, and exposed directly, if $^{32}$P-was used as label. Approximate exposure times for visualizing low specific activity transcripts (for example, if 1 µl of 800 Ci/mMole, 10 mCi/ml $^{32}$P-UTP was used in the MEGAscript reaction) are about 10–30 minutes with an intensifying screen, or several hours-overnight without a screen, if 1 µl of the undiluted reaction is run on the gel. A recipe for a standard denaturing (i.e. 8 M urea) 5% polyacrylamide gel and Tris-borate-EDTA running buffer is given in the Appendix.

B. Determination of Yield of Transcription Products

The yield of RNA transcripts synthesized can be determined by TCA (trichloroacetic acid) precipitation if a radio-labeled nucleotide tracer (for example, $^{32}$P-UTP) is included in the reaction. After termination of the reaction (or at any time during the reaction), an aliquot (about 1 µl) is removed and thoroughly mixed with 100 µl of TE buffer or RNase-free dH$_2$O. Half of the diluted RNA sample is added to a 12×75 mm glass tube containing RNase-free carrier (for example, 50 ug of yeast RNA or sonicated fish sperm DNA) in a volume about 100 µl, mixed, and then added to 2 ml of 10% TCA is added. The tube is vortexed briefly and placed on ice for 5 minutes. The precipitated nucleic acid is then collected by vacuum filtration through a glass fiber filter that has been wet with TCA. The filter is then rinsed successively with 10% TCA and ethanol. The filter is added to scintillation cocktail and counted. (When using tolulene-based scintillation cocktails, the filter should be dried before counting.) The other half of the diluted RNA is added directly to an aqueous scintillation cocktail and counted. The ratio of the two values is the fraction of labeled nucleotide incorporated into RNA. At a total ribonucleotide concentration of 30 mM (7.5 mM of each of the four NTP's) in a 20 µl reaction, each 1% incorporation corresponds to about 2 µg of RNA synthesized.

Calculation of yield

In a standard MEGAscript reaction containing a 7.5 mM concentration of each of the four ribonucleotide triphosphates in a 20 µl volume (corresponding to using 2 µl of each of the 4 ribonucleotide solutions), the total amount of NTP's in the reaction is 198 Ag (since the sum of the molecular weights of the 4 NTP's is 1320):

$$\frac{7.5 \text{ mM}}{10^6 \text{ µl}} \times \frac{1320 \text{ gm}}{1000 \text{ mM}} \times \frac{20 \text{ µl}}{1} =$$

$$\frac{1.98 \times 10^5 \text{ gm}}{10^9} = 1.98 \times 10^{-4} \text{ gm} = 198 \text{ µg}$$

If the TCA precipitation data shows 50% incorporation of a $^{32}$P-UTP tracer, the yield of RNA is 198 µg×50%=99 µg. When assessing yield of RNA by TCA precipitation, it is important to keep in mind that the yield is based on the fraction of label incorporated and the ratio of labeled nucleotide:unlabeled nucleotide (for example, $^{32}$P-UTP: unlabeled UTP). When in vitro transcription reactions are used to make high specific activity probes, the ratio of $^{32}$P-UTP: unlabeled UTP is typically about 1:8 (for example, if 1 µl of 800 Ci/mMole $^{32}$P-UTP at 10 mCi/ml is added to a 20 µl reaction containing a 5 µM concentration of unlabeled UTP). In contrast, in a standard MEGAscript reaction containing the same amount of $^{32}$P-UTP but with a 7.5 mM concentration of unlabeled UTP, the ratio of $^{32}$P-UTP: unlabeled UTP is 1:12,000. Therefore, for a given percent incorporation of $^{32}$P-UTP, the yield of RNA is 1500-fold greater in the MEGAscript reaction than in the probe synthesis reaction. (Since the mass amount of $^{32}$P-UTP in the MEGAscript reaction is negligible compared to be mass amount of unlabeled UTP, it can be disregarded in calculating the yield, as in the above example.)

An alternative method for quantitating the RNA synthesized is by ultraviolet light absorption, provided the DNA template and unincorporated nucleotides are first removed. An aliquot of the RNA is diluted and read in a microcuvette at 260 nm and 280 nm. An absorbance of one at 260 nm corresponds to an RNA concentration of 40 µg/ml, and the ratio of the absorbance values at 260 nm and 280 nm should be in the range of 1.8–2.

C. Synthesis of Capped RNA Transcripts

Most mRNA molecules have a 5' 7 methyl guanosine residue or cap which functions both in the protein synthesis initiation process and also serves to protect the mRNA from nuclease digestion intracellular. Capped in vitro transcripts can be synthesized by adding cap analog directly to the transcription reaction. It is frequently not necessary to cap in vitro transcripts for in vitro translation experiments. Geravitik et al point out that the yield of in vitro translation experiments with uncapped in vitro transcripts can equal that of capped transcripts by increasing the amount of uncapped transcript added to the translation reaction and decreasing the K$^+$ concentration. Ambion's Retic Lysate IVT™ translation kit is supplied with alternative buffers optimized for translating uncapped in vitro transcripts.

In vitro transcripts which are to be microinjected into oocytes or other cells, or for transfection experiments or in vitro splicing reactions, should be capped. However, there are several factors which should be considered. These are that cap analog is a relatively expensive reagent, reactions which contain cap analog have significantly lower yields and unincorporated cap analog is a potent inhibitor of protein synthesis initiation. (Kreig and Melton, 1987) The standard strategy to synthesize capped transcripts is to reduce the level of GTP to 1/10 the normal concentration and replace this with cap analog. This results in a high proportion of the transcripts being capped. Unfortunately it also significantly decreases the yield of the transcription reaction often to 20% or lower. To conserve cap analog and increase the efficiency of the transcription reaction many workers have been decreasing the ratio of cap analog to GTP. Four to one cap:GTP is frequently used, although we have heard of people using 1:1. It is likely, however, that the fraction of capped mRNA molecules decreases as the ratio of cap to GTP decreases. Thus, depending on your specific requirements we recommend using a four to one ratio of cap analog to GTP unless it is essential that almost all of the transcripts be capped. The concentration of GTP in SP6 polymerase reactions is normally 5 mM and for T7 and T3 7.5 mM. The nucleotide stocks for SP6 kits are 50 mM and for T7 and T3 kits, 75 mM. A portion of the GTP stock should be mixed with 4 parts water and 2 µl of the 1:4 diluted GTP added to a 20 µl reaction. 2 µl of a 40 mM stock of cap analog should be added to a 20 µl SP6 reaction and 3 µl for 20 µl T7 or T3 reactions. The remainder of the reaction should be assembled as usual.

D. Transcription of PCR Products Containing Phage Promoters

By using primers which flank the phage promoter(s) in the transcription vector, an inserted DNA fragment can be amplified and used directly as the template in a MEGAscript reaction. Alternatively, the phage promoter sequence can be appended to one of the PCR primers and incorporated into the PCR product. Often the amplified DNA can be used directly in the transcription reaction with no purification after the PCR. Typically, 5 µl of a 100 µl PCR, corresponding to about 0.5 µg of double-stranded DNA, is used as a template in the standard MEGAscript reaction. If the yield of RNA is low, it may be necessary to purify the amplified DNA before use to remove inhibitors, for example by one of the procedures that use binding to and elution from glass particles, or by phenol/chloroform extraction and ethanol precipitation.

V. Troubleshooting

The amount of RNA synthesized in a standard MEGAscript reaction should be at least 50 µg and often exceeds 100 µµg. If the yield is low, the first step for troubleshooting the reaction is to perform the standard MEGAscript reaction using 2 µl of the control template solution provided with the kit. The yield of RNA from the control T7 polymerase reaction should be at least 100 µg of transcript, 1700 nt in length, which would correspond to 50% incorporation of a $^{32}$P-NTP added as a tracer. If the yield of RNA from the control reaction is low, either something is wrong with the procedure, something is wrong with the kit, or the quantitation is in error. To confirm that the quantitation is correct, try to verify the yield by an independent method, for example if TCA precipitation was used to assess yield, try also running an aliquot of the reaction on an agarose gel. If the yield is indeed low by two independent methods of assessment, there may be a technical problem with the way the kit is being used. For example, the spermidine in the 10×Transcription Buffer may cause precipitation of the template DNA if these components are not diluted by the prior addition of the other ingredients in the reaction. (This is the reason that the water is added first.) Repeat the reaction, paying close attention to detail in the New Users protocol.

If the control reaction results in a satisfactory yield of RNA but the yield with your template is low, you should run the control reaction again, using both the control template and a mixture of your template and the control template. If the control reaction is inhibited in the presence of your template, you need to take steps to remove inhibitors from your template DNA preparation. These steps could include, for example, purifying your template on a CsCl gradient (make sure all CsCl is removed, by dialysis or several rounds of ethanol precipitation and washing the pellet), or by a glass particle purification procedure. Another method of removing protein inhibitors is to treat the DNA with proteinase K (100 µg/ml) and SDS (0.5%) for 30 minutes at 37° C., followed by phenol/chloroform extraction and ethanol precipitation. There are a number of contaminants which can cause problems with template DNA. The most common is residual RNase from a plasmid miniprep. If RNase is used in the miniprep procedure, it is essential that a Proteinase K digestion and phenol/$CHCl_3$ extraction to be used to eliminate all RNase before transcription. A second problem is DNA contaminated with residual SDS. This is generally removed by phenol/$CHCl_3$ extraction and ethanol precipitation. Carryover of SDS can be minimized by diluting the nucleic acid several-fold before ethanol precipitation.

Phage RNA polymerases are inhibited by high NaCl concentration, so it is important that significant amounts of salt are not introduced into the transcription reaction with the template DNA. A 70% ethanol wash of the DNA pellet will remove most residual salt.

If addition of your template to the MEGAscript reaction containing the control template does not inhibit synthesis of the control RNA, the problem may be intrinsic to your template. Templates differ in their transcription efficiencies depending on their intrinsic affinity for the polymerase, the presence of internal termination signals, and their length. If the problem is due to internal termination signals subcloning the fragment to be transcribed into a vector having a different phage promoter may alleviate the problem. Another possibility is that the quantitation of your template is in error. If quantitation was based on uv absorbance and your DNA prep had substantial amounts of RNA or chromosomal DNA, the amount of template DNA may be substantially less than the calculated value. Also, check an aliquot of your template DNA on an agarose gel to make sure it is not degraded and is of the expected size. In some cases, yields can be improved by using more or less than the standard 1 µg recommended amount of template. If the template is very large, you may need to use more to keep the concentration of promoters at a reasonable level (a 2 kb template in a 2.5 Kb vector will have only approximately 60% of the promoters per unit weight as a 300 bp template in the same vector. Another parameter that can be adjusted is reaction time. Extending the standard 4 hour incubation to 6 hours or even overnight sometimes improves yields. One concern about extending the incubation time is that if there is any ribonuclease in the reaction and it is kept in check by the placental RNase inhibitor contained in the Enzyme Mix, the RNase may be slowly released after extended incubation, resulting in degradation of the RNA.

Finally, if the yield is O.K. but the size of the product is unexpected, consider that the RNA may be running aberrantly due to secondary structure. Sometimes the RNA will run as two distinct bands on a native agarose gel, one band being smaller than anticipated, but when the same RNA is run on a denaturing polyacrylamide gel, it will migrate as a single band of the expected size.

VI Appendix

A. 10×TBE Gel Running Buffer:
   Composition of 10×Buffer:

| | |
|---|---|
| 0.9 M Tris | 1. 109 g Tris base |
| 0.89 M boric acid | 2. 55 g boric acid |
| 20 mM EDTA | 3. 40 ml 0.5M EDTA pH8 |
| | 4. distilled/deionized H$_2$O to |
| | 1 liter |

1 liter

B. 5% acrylamide /8M urea gel (for 15 ml, enough for a 13 cm×15 cm×0.75 mm thick gel):
   1. 7.2 $\mu$m high-quality urea
   2. 1.5 ml 10×TBE
   3. 2.5 ml 30% acrylamide (acrylamide: bis acrylamide= 19:1)
   4. dH$_2$O to 15 ml—stir at room temperature until urea has dissolved; add
   5. 120 $\mu$l of 10% ammonium persulfate in dH$_2$O
   6. 16 $\mu$l TEMED—mix briefly after adding the last two ingredients, which will catalyze polymerization, then pour gel immediately.

C. RNase—free Water:
   Add diethylpyrocarbonate to double-distilled, deionized H$_2$O to a concentration of 0.1% (i.e. add 1 ml per liter of H$_2$O); shake well, incubate several hours—overnight at 37° or 42°; autoclave at least 45 minutes, or until DEP scent is gone.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The references listed below are incorporated herein by reference to the extent that they supplement, explain, provide a background for or teach methodology, techniques and/or compositions employed herein.

Current Protocols in Molecular Biology Eds F. M. Ausubel, R.

Brent,. R. E. Kingston, D. D. Moore, J. G. Seidman., J. A. Smith and K. Struhl. J. Wiley & Sons New York (1989).

Browning, K. S. 1989. Transcription and translation of mRNA from polymerase chain reaction-generated DNA. Amplifications 3:14–15.

Butler, E. T., Chamberlin, M. J. (1982) Bacteriophage SP6-specific RNA polymerase. J. of Biol. Chem. 257, 10, 5772–5778.

Chamberlin, M. and Ring, J. (1973) Characterization of T7-specific ribonucleic acid polymerase. J. Biol. Chem. 218, 2235–2244.

Chamberlin, M. J. and Rhodes, G. (1974) Ribonucleic acid chain elongation by *Escherichia coli* ribonucleic acid polymerase. J. Biol. Chem. 249,6675–6683.

Cunningham, P. R. and Ofengand, J. (1990) Use of inorganic pyrophosphatase to improve the yield of in vitro transcription reactions catalyzed by T7 RNA polymerase. Biotechniques 9, 713–714.

Ehrlich, Ed. PCR Technology Stockton Press, New York (1989) The Design & Optimization of the PCR. Saki, R. K. pg 7–16.

Fahy, E., Kwoh, D. Y., Gingeras, T. R. (1991) Self-sustained Sequence Replication (3SR): An Isothermal Transcription-based Amplification System Alternative to PCR. PCR 1, 25–33.

Gurevich, V. V., Pokrovskaya, I. D., Obukhova, T. A., and Zozulya, S. A. (1991). Preparative in vitro mRNA synthesis using SP6 and T7 RNA polymerases. Anal. Biochem 195, 207–213.

Hinton, D. M., Brennan, C. A., Gumport, R. I. (1982) The Preparative Synthesis of Oligodeoxyribonucleotides using RNA Ligase. Nucl. Acids Res. 10–6, 1877–1874.

Kreig, P. A. and Melton, D. A. 1987. In vitro RNA Synthesis with SP6 RNA Polymerase. Methods in Enzymology. 155:397–415.

Milligan, J. F., Groebe, D. R., Witherell, G. W. and Uhlenbeck, O. C. (1987) Oligoribonucleotide synthesis using T7 RNA polymerase and synthetic DNA templates. Nucl. Acids Res. 15, 8783–8798.

Milligan, J. F., and Uhlenbeck, O. C. (1989) Synthesis of small RNAs using T7 RNA polymerase. Methods in Enzymology, 180, 51–62.

Sampson, J. R. and Uhlenbeck, O. C. (1988) Biochemical and physical characterizations of an unmodified yeast phenylalanine transfer RNA transcribed in vitro. Proc. Natl. Acad. Sci. USA 85, 1033–1037.

Schenborn, E. T. and Mierindorf, R. C. 1985. A novel transcription property of SP6 and T7 RNA polymerases: dependence on template structure. Nucl. Acids Res. 13:6223–6236.

Tabor, S. and Richardson, C. C. (1990) J. Biol. Chem. 265, 8322–8328.

Verhoevern, J. A., Schenk, K. M., Meyer, R. R., Trela, J. M. (1986) Purification & Characterization of an Inorganic Pyrophosphatase from the Extreme Thermophile Thermus Aquaticus. J. Bacteriol. 168(1), 318–321.

Weitzmann, C. J., Cunningham, P. R. and Ofengand, J. (1990) Cloning, in vitro transcription, and biological activity of *Escherichia coli* 23S ribosomal RNA. Nucl. Acids Res. 18, 3515–3520.

Wyatt, J. R., Chastain, M. and Puglisi, J. D. (1991) Synthesis and purification of large amounts of RNA oligonucleotides. Biotechniques 11, 764–769.

What is claimed is:

1. A method of preparing a polynucleotide, comprising:
   (a) preparing a reaction mixture comprising:
      an initial total nucleotide concentration of greater than 16 mM;
      an initial free Mg$^{++}$ concentration equal to or less than 0.2 mM;
      inorganic pyrophosphatase;
      a polynucleotide template; and
      an RNA polymerase; and
   (b) incubating the reaction mixture to produce a polynucleotide.

2. The method of claim 1, wherein the free Mg$^{++}$ concentration remains equal to or less than 0.2 mM throughout incubation.

3. The method of claim 1, wherein the free $Mg^{++}$ concentration does not remain equal to or less than 0.2 mM throughout incubation.

4. The method of claim 1, wherein the reaction mixture is further defined as comprising an initial molar concentration of $Mg^{++}$ that is not more than 10% greater than the total molar nucleotide concentration.

5. The method of claim 4, wherein the initial total molar concentration of $Mg^{++}$ is less than the initial molar total nucleotide concentration.

6. The method of claim 1, wherein the initial total nucleotide concentration is less than 40 mM.

7. The method of claim 1, wherein the reaction mixture is further defined as comprising an initial total nucleotide concentration of about 16 mM.

8. The method of claim 1, wherein the reaction mixture is further defined as comprising an initial total nucleotide concentration of about 20 mM.

9. The method of claim 1, wherein the reaction mixture is further defined as comprising an initial total nucleotidle concentration of about 30 mM.

10. The method of claim 1, wherein the reaction mixture is further defined as comprising an initial total nucleotide concentration of about 40 mM.

11. The method of claim 1, wherein the initial total nucleotide concentration is between 16 mM and 40 mM.

12. The method of claim 11, wherein the initial total nucleotide concentration is between 20 mM and 40 mM.

13. The method of claim 12, wherein the initial total nucleotide concentration is between 30 mM and 40 mM.

14. The method of claim 11, wherein the initial total nucleotide concentration is between 16 mM and 30 mM.

15. The method of claim 14, wherein the initial total nucleotide concentration is between 20 mM and 30 mM.

16. The method of claim 11, wherein the initial total nucleotide concentration is between 16 mM and 20 mM.

17. The method of claim 11, wherein at least one nucleotide is present in a form other than as a compound with $Na^+$, $Li^+$, $K^+$, $Ba^{++}$, or $NH_4^+$.

18. The method of claim 1, wherein at the least one nucleotide is a Mg-nucleotide.

19. The method of claim 17, wherein at least one wherein at the least one nucleotide is a Tris-nucleotide.

20. The method of claim 1, wherein the RNA polymerase enzyme is a bacteriophage RNA polymerase.

21. The method of claim 20, wherein the bacterial RNA polymerase is T7 RNA polymerase, T3 RNA polymerase, or SP6 RNA pdlymerase.

22. The method of claim 21, wherein the bacterial RNA polymerase is T7 RNA polymerase.

23. The method of claim 21, wheiein the bacterial RNA polymerase is T3 RNA polynerase.

24. The method of claim 21, wherein the bacterial RNA polymerase is SP6 RNA polymerase.

25. A reaction mixture comprising:

an initial total nucleotide concentration of greater than 16 mM;

an initial free $Mg^{++}$ concentration equal to or less than 0.2 mM;

inorganic pyrophosphatase; and an RNA polymerase enzyme.

26. The reaction mixture of claim 25, further defined as comprising an initial total nucleotide concentration of less than 40 mM.

* * * * *

UNITED STATES PATENT AND TRADEMARK OFFICE
CERTIFICATE OF CORRECTION

PATENT NO.     : 6,586,218 B2
DATED          : July 1, 2003
INVENTOR(S)    : Milbum et al.

It is certified that error appears in the above-identified patent and that said Letters Patent is hereby corrected as shown below:

Title page,
Item [57], ABSTRACT
Lines 6 and 7, delete "synthesised" and replace -- synthesized -- therefor.

Column 31,
Line 20, delete "nucleotidle" and insert -- nucleotide -- therefor.

Column 32,
Line 3, delete "claim 11" and insert -- claim 1 -- therefor.
Line 6, delete "claim 1" and insert -- claim 17 -- therefor.

Signed and Sealed this

Twenty-third Day of March, 2004

JON W. DUDAS
*Acting Director of the United States Patent and Trademark Office*